US012740938B2

(12) United States Patent
Sanchez et al.

(10) Patent No.: US 12,740,938 B2
(45) Date of Patent: Sep. 22, 2026

(54) TOPICAL COMPOSITION AGAINST FINE LINES AND WRINKLES

(71) Applicant: MARY KAY INC., Addison, TX (US)

(72) Inventors: Milagros Sanchez, Addison, TX (US); Geetha Kalahasti, Addison, TX (US); Barbara Durkee, Addison, TX (US)

(73) Assignee: MARY KAY INC., Addison, TX (US)

( * ) Notice: Subject to any disclaimer, the term of this patent is extended or adjusted under 35 U.S.C. 154(b) by 277 days.

(21) Appl. No.: 18/573,357

(22) PCT Filed: Jul. 1, 2022

(86) PCT No.: PCT/US2022/073353

§ 371 (c)(1),
(2) Date: Dec. 21, 2023

(87) PCT Pub. No.: WO2023/279086

PCT Pub. Date: Jan. 5, 2023

(65) Prior Publication Data

US 2024/0285513 A1 Aug. 29, 2024

Related U.S. Application Data

(60) Provisional application No. 63/217,625, filed on Jul. 1, 2021.

(51) Int. Cl.

| | |
|---|---|
| ***A61K 8/9789*** | (2017.01) |
| ***A61K 8/06*** | (2006.01) |
| ***A61K 8/34*** | (2006.01) |
| ***A61K 8/39*** | (2006.01) |
| ***A61K 8/49*** | (2006.01) |
| ***A61Q 19/08*** | (2006.01) |

(52) U.S. Cl.
CPC ............ *A61K 8/9789* (2017.08); *A61K 8/062* (2013.01); *A61K 8/34* (2013.01); *A61K 8/345* (2013.01); *A61K 8/39* (2013.01); *A61K 8/4973* (2013.01); *A61Q 19/08* (2013.01); *A61K 2800/782* (2013.01)

(58) Field of Classification Search
None
See application file for complete search history.

(56) References Cited

FOREIGN PATENT DOCUMENTS

| | | |
|---|---|---|
| CN | 109602668 | 4/2019 |
| EP | 0641557 | 3/1995 |
| WO | WO 2015/167560 | 11/2015 |
| WO | WO 2020/009937 | 1/2020 |

OTHER PUBLICATIONS

Database GNPD [Online] MINTEL: Apr. 12, 2017, anonymous: “Face Serum”, XP055973610, Database accession No. 4737679.
International Search Report and Written Opinion issued in Corresponding PCT Application No. PCT/US2022/073353, dated Nov. 2, 2022.

*Primary Examiner* — Michael V Meller
(74) *Attorney, Agent, or Firm* — NORTON ROSE FULBRIGHT US LLP

(57) ABSTRACT

Topical skin compositions and methods for their use are disclosed. The compositions can include at least one skin active ingredient capable of treating a skin condition, and a plurality of skin penetration enhancers capable of increasing the penetration of the skin active into the skin. The plurality of skin penetration enhancers can include alcohol, dimethyl isosorbide, pentylene glycol, ethoxydiglycol, and propylene glycol.

16 Claims, 5 Drawing Sheets

* p<0.05 for mean response relative to baseline

* p<0.05 for mean score relative to baseline

* $p<0.05$ for mean score relative to baseline

TOPICAL COMPOSITION AGAINST FINE LINES AND WRINKLES

CROSS-REFERENCE TO RELATED APPLICATIONS

This application is a national phase under 35 U.S.C. § 371 of International Application No. PCT/US2022/073353, filed Jul. 1, 2022, which claims the benefit of priority to U.S. Provisional Patent Application Ser. No. 63/217,625, filed Jul. 1, 2021, the entire contents of each of which are hereby incorporated by reference in their entireties.

BACKGROUND OF THE INVENTION

A. Field of the Invention

The present invention relates generally to a cosmetic skin care composition that is able to reduce the appearance of fine lines or wrinkles on a person's skin. The composition can include at least one skin active ingredient and a plurality of skin penetration enhancers capable of increasing the penetration of the skin active into the skin.

B. Description of Related Art

Certain types of wrinkles develop over time on facial skin due to repetitive muscle contraction. These types of wrinkles are typically referred to as rhytides, examples of which can include frown or glabellar lines, forehead lines, crow's feet, bunny or nasalis lines, dimpled chin, smile lift lines, lip lines, etc. Currently, a wide variety of commercially available treatment materials are available and are purportedly effective as facial muscle relaxants/muscle contraction suppressants. These materials are said to be capable of reducing the appearance of such wrinkles. Non-limiting examples of such treatment materials include injectable neuromodulators such as Botox® (onabotulinumtoxinA), Dysport® (abobotulinumtoxinA), or Xeomin® (incobotulinumtoxinA). Other examples include topically administered treatment materials such as chemical compounds (e.g., gamma-aminobutyric-acid) and peptides (e.g., acetyl hexapeptide-3).

Various problems are associated with injectable neuromodulators, such as allergic reactions, rash, itching, injection site reactions (bruising, bleeding, pain, redness, swelling, or tenderness), muscle stiffness, fever, cough, sore throat, flu-like symptoms, neck or back pain, and the potential to spread from the injection site to other parts of the body, resulting in serious risks including difficulty talking, swallowing or breathing, muscle weakness, drooping eyelids, and blurred or double vision. Similarly, chemical compounds have their own drawbacks such as skin irritation and potential allergic reactions. Aside from the physiological problems associated with injectable neuromodulators and chemical compounds, these elective cosmetic procedures can be cost-prohibitive for a large segment of the population who may benefit.

There have been attempts to produce natural-based ingredients that have the ability to relax facial muscles. While these natural-based ingredients may offer some muscle relaxation effects, oftentimes there can be an issue of delivering such ingredients into the skin. In particular, an effective amount of a natural-based ingredient may not be capable of penetrating the surface of the skin and/or being delivered to the epidermal or dermal layers of the skin or to muscle cells within or below such skin layers.

Thus, previous attempts to improve the visual appearance of skin have been shown to have various drawbacks such as high costs, medical risks, skin irritation, prolonged recovery periods, or inefficient delivery of the promised skin benefits.

SUMMARY OF THE INVENTION

A solution has been identified to at least one of the aforementioned problems. In one aspect of the present invention, the solution can include the use of a combination of skin penetration enhancers that can increase the delivery of a skin active ingredient to the epidermal and/or dermal layers of the skin and/or to muscle cells present within such layers or muscle cells located below such layers of the skin. The combination of skin penetration enhances capable of increasing the penetration of the skin active ingredient into the skin can include alcohol, dimethyl isosorbide, pentylene glycol, ethoxydiglycol, and propylene glycol. In some particular embodiments, the compositions of the present invention can include 5 to 15% by weight of alcohol, 5 to 15% by weight of dimethyl isosorbide, 3 to 7% by weight of pentylene glycol, 1 to 5% by weight of ethoxydiglycol, and 1 to 5% by weight of propylene glycol.

In one aspect of the present invention, there is disclosed a method of improving the appearance of a person's skin. In some embodiments, the method comprises topically applying a topical skin composition comprising at least one skin active ingredient capable of treating a skin condition and a plurality of skin penetration enhancers capable of increasing the penetration of the skin active into the skin. In some embodiments, the plurality of skin penetration enhancers include, alcohol, dimethyl isosorbide, pentylene glycol, ethoxydiglycol, and propylene glycol. In some embodiments, the at least one skin active ingredient is capable of reducing muscle contraction of a facial muscle in a person and/or reducing the appearance of a fine line or wrinkle on a person's skin. In some embodiments, the at least one skin active ingredient is *Acmella oleracea* extract, *Lavandula stoechas* extract, or *Rosmarinus officinalis* leaf extract. In some embodiments, the composition comprises *Acmella oleracea* extract, *Lavandula stoechas* extract, and *Rosmarinus officinalis* leaf extract. In some embodiments, the composition comprises 0.02 to 2% by weight of *Acmella oleracea* extract, 0.01 to 1% by weight of *Lavandula stoechas* extract, and 0.005 to 0.5% by weight of *Rosmarinus officinalis* leaf extract. In some embodiments, the *Acmella oleracea* extract stimulates collagen production and laminin production in the skin. In some embodiments, the *Rosmarinus officinalis* leaf extract reduces matrix metalloproteinases 1, 3, or 9 production in the skin.

In some embodiments, each of the extracts is individually an aqueous extract, an alcohol extract, a polyol extract, or a combination thereof. In some embodiments, the *Rosmarinus officinalis* leaf extract is obtained with a fluid extraction solvent mixture comprising betaine, lactic acid, and water. In some embodiments, the *Lavendula stoechas* extract is a *Lavendula stoechas* flower/leaf/stem extract obtained with a supercritical carbon dioxide ($CO_2$) extraction solvent. In some embodiments, the *Acmella oleracea* extract is obtained with a fluid extraction solvent mixture comprising water, ethanol, and 1,3 propanediol.

In some embodiments, the composition comprises 5 to 15% by weight of alcohol, 5 to 15% by weight of dimethyl isosorbide, 3 to 7% by weight of pentylene glycol, 1 to 5% by weight of ethoxydiglycol, and 1 to 5% by weight of propylene glycol. In some embodiments, the composition comprises 30 to 60% by weight of water. In some embodiments, the composition further comprises cetyl esters, stearyl alcohol, cetearyl olivate, sorbitan olivate, acrylates/C10-30 alkyl acrylate crosspolymer, cetyl palmitate, and sorbitan palmitate. In some embodiments, the composition further comprises 3 to 7% by weight of cetyl esters, 1 to 5% by weight of stearyl alcohol, 1 to 5% by weight of cetearyl olivate, 1 to 5% by weight of sorbitan olivate, 0.1 to 1% by weight of acrylates/C10-30 alkyl acrylate crosspolymer, 0.1 to 1% by weight of cetyl palmitate, and 0.1 to 1% by weight of sorbitan palmitate.

In some embodiments, the composition is an emulsion. In some embodiments, the emulsion is an oil-in-water emulsion. In some embodiments, the composition is applied to a fine line or wrinkle. In some embodiments, the appearance of the fine line or wrinkle is reduced after topical application. In some embodiments, the composition reduces muscle contraction of a muscle that causes the appearance of the fine line or wrinkle. In some embodiments, the facial muscle is a glabellar complex muscle, an orbicularis oculi muscle, a depressor muscle, or a *frontalis* muscle, or any combination thereof. In some embodiments, the fine line or wrinkle is a rhytide. In some embodiments, the facial skin is forehead skin, cheek skin, chin skin, and/or orbital area skin.

In some embodiments, the composition is applied directly to a subject's skin. In some embodiments, applying the composition to a subject's skin will increase skin firmness and tonicity, reduce oxidative stress, reduce skin free-radical content, reduce the appearance of lines and/or wrinkles, reduce skin sagging, reduce dermatological signs of chronological aging and photo-aging, minimize dermatological signs of fatigue and/or stress, and/or resurface the subject's skin. In some embodiments, the composition is provided in the form of an emulsion.

Some aspects of the disclosure are directed to improving a condition or appearance of skin, comprising applying any one of the compositions disclosed herein to skin in need thereof. In one aspect, any one of the compositions disclosed herein is applied to skin and the composition is left on the skin, or alternatively removed from the skin after a period of time. In some aspects, the compositions disclosed herein are used to treat and/or reduce wrinkles. In some aspects, the compositions disclosed herein are used to increase skin firmness and tonicity. In some aspects, the compositions disclosed herein are used to reduce oxidative stress and skin free-radical content.

In some aspects, the compositions of the present invention are formulated as a topical skin composition. The composition can be formulated for topical skin application at least 1, 2, 3, 4, 5, 6, 7, or more times a day during use. In other aspects of the present invention, compositions can be storage stable. It is also contemplated that the degree of dissolution of the composition can be selected to achieve a desired result, e.g., depending on the type of composition desired. In some embodiments, the composition is applied directly to the skin.

In some aspects, the compositions of the present invention can further include a surfactant, a silicone containing compounds, a UV agent, an oil, and/or other ingredients identified in this specification or those known in the art. The composition can be a lotion, cream, body butter, mask, scrub, cleanser, cream, toner, wash, gel, serum, emulsion (e.g., oil-in-water, water-in-oil, silicone-in-water, water-in-silicone, water-in-oil-in-water, oil-in-water-in-oil, oil-in-water-in-silicone, etc.), solutions (e.g., aqueous or hydro-alcoholic solutions), anhydrous bases (e.g., lipstick or a powder), ointments, milk, paste, aerosol, solid forms, eye jellies, gel serums, gel emulsions, etc. The composition can be formulated for topical skin application at least 1, 2, 3, 4, 5, 6, 7, or more times a day during use. In some aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, cps, etc., as measured on a Brookfield Viscometer using a TC spindle at 2.5 rpm at 25° C.).

The compositions, in non-limiting aspects, can have a pH of about 6 to about 9. In some aspects, the pH can be 1, 2, 3, 4, 5, 6, 7, 8, 9, 10, 11, 12, 13, or 14. The compositions can include a triglyceride. Non-limiting examples include small, medium, and large chain triglycerides. In certain aspects, the triglyceride is a medium chain triglyceride (e.g., caprylic capric triglyceride). The compositions can also include preservatives. Non-limiting examples of preservatives include phenoxyethanol, methylparaben, propylparaben, iodopropynyl butylcarbamate, potassium sorbate, sodium benzoate, or any mixture thereof. In some embodiments, the composition is paraben-free.

Compositions of the present invention can have UVA and UVB absorption properties. The compositions can have a sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The compositions can be sunscreen lotions, sprays, creams, toners, serums, cleansers, or masks.

The compositions of the present invention can also include any one of, any combination of, or all of the following additional ingredients: a conditioning agent, a moisturizing agent, a pH adjuster, a structuring agent, inorganic salts, a preservative, a thickening agent, a silicone containing compound, an essential oil, a fragrance, a vitamin, a pharmaceutical ingredient, or an antioxidant, or any combination of such ingredients or mixtures of such ingredients. In certain aspects, the composition can include at least two, three, four, five, six, seven, eight, nine, ten, or more, or all of these additional ingredients identified in the previous sentence. Non-limiting examples of these additional ingredients are identified throughout this specification and are incorporated into this section by reference. The amounts of such ingredients can range from 0.0001% to 99.9% by weight or volume of the composition, or any integer or range in between as disclosed in other sections of this specification, which are incorporated into this paragraph by reference.

It is also contemplated that the compositions disclosed throughout this specification can be used as a leave-on or rinse-off composition. By way of example, a leave-on composition can be one that is topically applied to skin and remains on the skin for a period of time (e.g., at least 5, 6, 7, 8, 9, 10, 20, or 30 minutes, or at least 1, 2, 3, 4, 5, 6, 7, 8, 9, 10, 11, 12, 13, 14, 15, 16, 17, 18, 19, 20, 21, 22, 23 or 24 hours, or overnight or throughout the day). Alternatively, a rinse-off composition can be a product that is intended to be applied to the skin and then removed or rinsed from the skin (e.g., with water) within a period of time such as less than 5, 4, 3, 2, or 1 minute. An example of a rinse off composition can be a skin cleanser, shampoo, conditioner, or soap. An example of a leave-on composition can be a skin moisturizer, sunscreen, mask, overnight cream, or a day cream.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, mist, dollop, or liquid. The container can include indicia on its surface. The indicia can be a word, an abbreviation, a picture, or a symbol.

It is contemplated that any embodiment discussed in this specification can be implemented with respect to any method or composition of the invention, and vice versa. Furthermore, compositions of the invention can be used to achieve methods of the invention.

In one embodiment, the compositions of the present invention can be pharmaceutically or cosmetically elegant or can have pleasant tactile properties. “Pharmaceutically elegant,” “cosmetically elegant,” and/or “pleasant tactile properties” describes a composition that has particular tactile properties which feel pleasant on the skin (e.g., compositions that are not too watery or greasy, compositions that have a silky texture, compositions that are non-tacky or sticky, etc.). Pharmaceutically or cosmetically elegant can also relate to the creaminess or lubricity properties of the composition or to the moisture retaining properties of the composition.

Also disclosed are the following Aspects 1 to 21 of the present invention.

Aspect 1 is a topical skin composition comprising at least one skin active ingredient capable of treating a skin condition, and a plurality of skin penetration enhancers capable of increasing the penetration of the skin active into the skin, wherein the plurality of skin penetration enhancers include: alcohol; dimethyl isosorbide; pentylene glycol; ethoxydiglycol; and propylene glycol. Aspect 2 is the topical skin composition of aspect 1, wherein the at least one skin active ingredient is capable of reducing muscle contraction of a facial muscle in a person and/or reducing the appearance of a fine line or wrinkle on a person's skin. Aspect 3 is the topical skin composition of aspect 1 or 2, wherein the at least one skin active ingredient is *Acmella oleracea* extract, *Lavandula stoechas* extract, or *Rosmarinus officinalis* leaf extract. Aspect 4 is the topical skin composition of any one of aspects 1 to 3 wherein the composition comprises *Acmella oleracea* extract, *Lavandula stoechas* extract, and *Rosmarinus officinalis* leaf extract. Aspect 5 is the topical skin composition of aspect 4, wherein the composition comprises 0.02 to 2% by weight of *Acmella oleracea* extract, 0.01 to 1% by weight of *Lavandula stoechas* extract, and 0.005 to 0.5% by weight of *Rosmarinus officinalis* leaf extract. Aspect 6 is the topical skin composition of any one of aspects 3 to 5, wherein each of the extracts is individually an aqueous extract, an alcohol extract, a polyol extract, or a combination thereof. Aspect 7 is the topical skin composition of any one of aspects 3 to 5, wherein the *Rosmarinus officinalis* leaf extract is obtained with a fluid extraction solvent mixture comprising betaine, lactic acid, and water; the *Lavendula stoechas* extract is a *Lavendula stoechas* flower/leaf/stem extract obtained with a supercritical carbon dioxide (CO2) extraction solvent; and the *Acmella oleracea* extract is obtained with a fluid extraction solvent mixture comprising water, ethanol, and 1,3 propanediol. Aspect 8 is the topical skin composition of any one of aspects 1 to 7, wherein the composition comprises: 5 to 15% by weight of alcohol; 5 to 15% by weight of dimethyl isosorbide; 3 to 7% by weight of pentylene glycol; 1 to 5% by weight of ethoxydiglycol; and 1 to 5% by weight of propylene glycol. Aspect 9 is the topical skin composition of any one of aspects 1 to 8, wherein the composition comprises 30 to 60% by weight of water. Aspect 10 is the topical skin composition of any one of aspects 1 to 9, wherein the composition further comprises: cetyl esters; stearyl alcohol; cetearyl olivate; sorbitan olivate; acrylates/C10-30 alkyl acrylate crosspolymer; cetyl palmitate; and sorbitan palmitate. Aspect 11 is the topical skin composition of aspect 10, wherein the composition further comprises: 3 to 7% by weight of cetyl esters; 1 to 5% by weight of stearyl alcohol; 1 to 5% by weight of cetearyl olivate; 1 to 5% by weight of sorbitan olivate; 0.1 to 1% by weight of acrylates/C10-30 alkyl acrylate crosspolymer; 0.1 to 1% by weight of cetyl palmitate; and 0.1 to 1% by weight of sorbitan palmitate. Aspect 12 is the topical skin composition of any one of aspects 1 to 11, wherein the composition is an emulsion. Aspect 13 is the topical skin composition of aspect 12, wherein the emulsion is an oil-in-water emulsion. Aspect 14 is a method of improving the appearance of a person's skin, the method comprising topically applying the composition of any one of aspects 1-13 to the person's skin, wherein the composition improves the appearance of the skin. Aspect 15 is the method of aspect 14, wherein the composition is applied to a fine line or wrinkle. Aspect 16 is the method of aspect 15, wherein the appearance of the fine line or wrinkle is reduced after topical application. Aspect 17 is the method of aspect 16, wherein the composition reduces muscle contraction of a muscle that causes the appearance of the fine line or wrinkle. Aspect 18 is the method of aspect 17, wherein the facial muscle is a glabellar complex muscle, an orbicularis oculi muscle, a depressor muscle, or a *frontalis* muscle, or any combination thereof. Aspect 19 is the method of any one of aspects 15 to 18, wherein the fine line or wrinkle is a rhytide. Aspect 20 is the method of any one of aspects 14 to 19, wherein the composition includes: *Acmella oleracea* extract, wherein the *Acmella oleracea* extract stimulates collagen production and laminin production in the skin; and *Rosmarinus officinalis* leaf extract, wherein the *Rosmarinus officinalis* leaf extract reduces matrix metalloproteinases 1, 3, or 9 production in the skin. Aspect 21 is the method of any one of aspects 14 to 20, wherein the facial skin is forehead skin, cheek skin, chin skin, and/or orbital area skin.

“Topical applying” means to apply a composition onto the surface of skin. Such compositions are typically dermatologically-acceptable in that they do not have undue toxicity, incompatibility, instability, allergic response, and the like, when applied to skin. Topical skin care compositions of the present invention can be formulated to achieve a targeted dissolution to avoid significant dripping after application to skin. The phrase “reducing the appearance of lines and/or wrinkles” refers to reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; reducing and/or diminishing the appearance and/or depth of lines and/or wrinkles; and/or improving the appearance of suborbital lines and/or periorbital lines.

The term “about” or “approximately” are defined as being close to as understood by one of ordinary skill in the art. In one non-limiting embodiment the terms are defined to be within 10%, preferably within 5%, more preferably within 1%, and most preferably within 0.5%.

The term "substantially" and its variations are refers to ranges within 10%, within 5%, within 1%, or within 0.5%.

The terms "inhibiting" or "reducing" or any variation of these terms includes any measurable decrease or complete inhibition to achieve a desired result. The terms "promote" or "increase" or any variation of these terms includes any measurable increase or production of a protein or molecule (e.g., matrix proteins such as collagen or elastin) to achieve a desired result.

The term "effective," as that term is used in the specification and/or claims, means adequate to accomplish a desired, expected, or intended result.

The use of the word "a" or "an" when used in conjunction with the terms "comprising," "including," "having," or "containing," or any variations of these terms, in the claims and/or the specification may mean "one," but it is also consistent with the meaning of "one or more," "at least one," and "one or more than one."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. With respect to the phrase "consisting essentially of," a basic and novel property of the compositions and methods of the present invention is a composition having a combination of skin penetration enhancers to increase delivery of a skin active ingredient into the skin (e.g., into the epidermal or dermal layers of the skin and/or to muscle cells present in or below such layers).

As used herein, the term "wrinkle" is a fold, ridge, crease, furrow, pit, crater, or sunken area in the skin that can be caused by habitual facial expressions, loss of collagen and/or elasticity due to aging, sun damage, smoking, poor hydration, and various other factors. A wrinkle can range from a deep crease to a fine line. Wrinkles occurring on any part of a body, in particular, wrinkles on head or neck of a subject are contemplated herein. Wrinkles that can be treated in accordance with the disclosure include, but are not limited to, a brow furrow, crows feet, nasolabial fold, one or more lines under the eyes or between the eye brows, and combinations thereof. Dynamic facial wrinkles and/or forehead wrinkles that are caused due to repetitive facial muscle contraction can include rhytides.

As used herein, "treatment" means to alleviate (or to eliminate) one or more features of a skin blemish either temporarily or permanently. When the compositions are administered to treat a wound, the compositions promote normal healing compared to a wound without the administration. That is, the size (length, depth, height and/or width), character, color and/or texture of the treated wound more closely resemble normal, non-wounded tissue. In this regard, treatment of a wound with the disclosed compositions can prevent, minimize or improve the appearance of a scar formation resulting from healing of the wound. Further, when the disclosed compositions are administered to treat a wrinkle, the wrinkle is treated if the appearance or prominence of the wrinkle is visibly or clinically diminished. That is the length and/or depth is decreased compared to the wrinkle prior to treatment. Alternatively, treatment can comprise prevention of a wrinkle. In this regard, the disclosed compositions can be applied to a region of the skin that typically develops a wrinkle, such as a forehead, lips, eyelids, nasolabial fold, skin under an eye, or between the eye brows in order to prevent the development of a wrinkle.

Other objects, features, and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DETAILED DESCRIPTION

Figure 1:
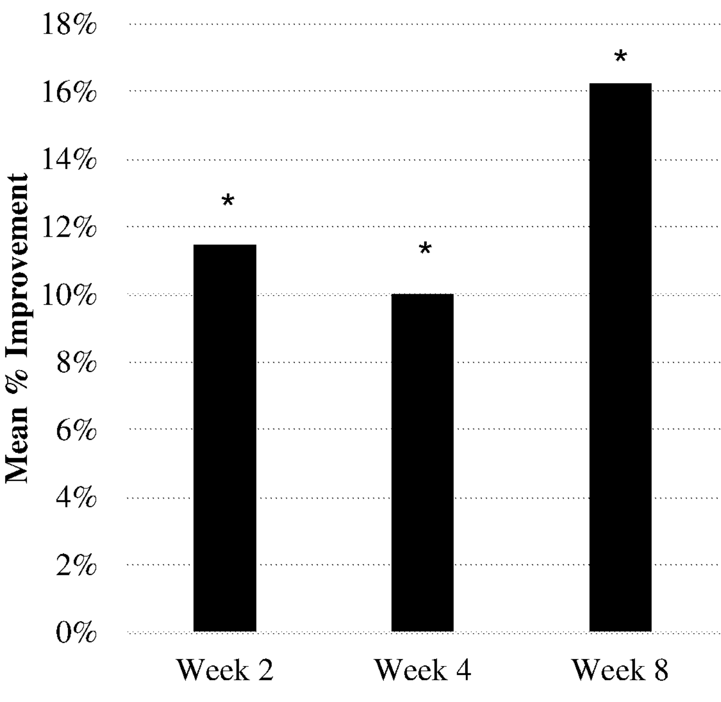
FIG. 1 provides data illustrating the mean % of improvement from baseline (0 week) in the EMG response area (mV.s) for muscle contraction in the *glabella* region for a group of people using a composition of the present invention having a combination of *Rosmarinus officinalis* leaf extract, *Lavendula stoechas* extract, and *Acmella oleracea* extract. The mean % of improvement illustrates reduced muscle contraction in the *glabella* region over time (2 weeks, 4 weeks, and 8 weeks). "*" indicates $p<0.05$ statistically significant improvement when compared to baseline (0 weeks).

As noted above, the present invention provides a solution to the problems associated with current cosmetic products. The solution is premised on the use of a combination of ingredients to reduce or reverse the appearance of wrinkles and additional aging-related signs. Skin wrinkling and laxicity or looseness are two primary events that affect skin appearance. Facial expression muscles in the periorbital, *glabella*, forehead, and perioral areas are involved in various expressions, including smiling, frowning, squinting, and pursing of the lips. The activity of these muscles places greater physical stress upon the overlying skin than in other areas in the face. Wrinkles form when these muscles contract beneath the skin then relax and return to their resting length. The overlying skin can also shorten and rebound, but not as well as the muscle. Therefore, the skin tends to buckle, fold inward, and form wrinkles as the muscles contract. The compositions disclosed herein include a wrinkle-relaxing component to counteract aging-related weakening of skin and wrinkling. The compositions also include antioxidants to protect the skin from oxidative stress stemming from ultraviolet sunlight and other environmental factors.

The following subsections describe non-limiting aspects of the present invention in further detail.

A. Penetration Enhancers

The compositions disclosed herein include a plurality of skin penetration enhancers capable of increasing the penetration of the skin active into the skin. The skin penetration enhancers include alcohol, dimethyl isosorbide, pentylene glycol, ethoxydiglycol, and propylene glycol. In cosmetics, alcohol is used for its high volatility (it disappears immediately after application), its drying, refreshing and antimicrobial properties. Alcohol facilitates the penetration of active ingredients into the superficial layers of the skin and promotes the deposit of ingredients on the skin. Dimethyl isosorbide is a solvent and carrier which offers a safe, effective delivery enhancement mechanism for active ingredients in personal care products. When used as a penetration enhancer, dimethyl isosorbide allows formulators to reduce the amount of actives required to achieve effects, resulting in reduced formulation costs, and lower skin irritation with aggressive active ingredients. Pentylene glycol is a humectant that has both moisture-binding and antimicrobial properties. Pentylene glycol is a 5-carbon organic compound that is miscible in water and can be used to enhance the absorption of organic compounds into the skin. Ethoxydiglycol promotes the dissolution of active organic components into formulations, which helps key ingredients work more effectively. Ethoxydoglycol also improves the texture or thickness of formulations, making them feel lighter and easier to spread. Propylene glycol is a humectant that is added to cosmetics to increase moisture retention in skin. When used in combination, these ingredients act as a carrier for active ingredients. They are readily absorbed into the skin and enhance absorption of active ingredients contained therein.

B. Active Ingredients

*Acmella oleracea* extract is an extract from the *Acmella oleracea* µlant. *Acmella oleracea* can be found in South America, Madagascar, and the Mascarene Islands. In a preferred instance, the *Acmella oleracea* extract is from the combination of the flower, leaf, and stem portions of *Acmella oleracea*. These portions can be combined and then crushed or macerated or crushed or macerated and then combined. The resulting crushed or macerated flower/leaf/stem material can then be subjected to a hydro-alcoholic (preferably hydro-ethanolic) extraction process or a hydro-alcoholic-polyol extraction process. The polyol in preferred instances can be 1,3-propanediol. The alcohol can be removed from the resulting extract. The *Acmella oleracea* extract can be then be used in the compositions of the present invention. In a preferred instance, the *Acmella oleracea* flower/leaf/stem extract can be obtained from a hydro-ethanol-1,3-propanediol solvent mixture. The resulting extract can then be used in the compositions of the present invention or can be further processed to remove the ethanol and can then be used in the compositions of the present invention. Alternatively, the extracting solvent can be a combination of water and polyol, preferably 1,3-propanediol, without an alcohol. The amounts of water, alcohol, and/or polyol present in the reaction mixture can be modified as desired. In some instances, *Acmella oleracea* extract is commercially available. In some instances, *Acmella oleracea* extract can be supplied by Gattefossé (France) under the trade name GATULINE® EXPRESSION AF. It was discovered in the context of the present invention that *Acmella oleracea* extract can reduce or inhibit contraction of myotubes by reducing or inhibiting an influx of calcium in the myotubes and reducing or preventing the occurrence of an action potential. It was also discovered that *Acmella oleracea* extract can increase both collagen production and laminin production in skin cells (e.g., keratinocytes or human dermal fibroblasts). *Acmella oleracea* extract include analgesic alkylamides such as splinthol that relax facial muscles and lessen muscle tension.

*Lavendula stoechas* extract is an extract from the plant *Lavendula stoechas*. *Lavendula stoechas* is native to the Mediterranean region, and is an evergreen shrub that is about 30 to 100 cm tall with greyish and tomentose leaves that are about 1 to 4 cm long. In a preferred instance, the *Lavendula stoechas* extract is from a combination of the flower, leaf, and stem portions of *Lavendula stoechas*. These portions can be combined and then crushed or macerated or crushed or macerated and then combined. The resulting crushed or macerated flower/leaf/stem material can then subjected to a supercritical extraction process using carbon dioxide ($CO_2$) as the solvent. The supercritical $CO_2$ extract of *Lavendula stoechas* flower/leaf/stem can then be used in the compositions of the present invention. The $CO_2$ supercritical extract of the *Lavendula stoechas* flower/leaf/stem can also be mixed with caprylic/capric triglycerides and then used in the compositions of the present invention. In some instances, *Lavendula stoechas* extract is commercially available. In some instances, *Lavendula stoechas* can be supplied by Barnet Products LLC (Englewood Cliffs, New Jersey (USA)) under the trade name STOCHEY'S. It was discovered in the context of the present invention that *Lavendula stoechas* extract can reduce or inhibit contraction of myotubes by reducing or inhibiting an influx of calcium in the myotubes and reducing or preventing the occurrence of an action potential. *Lavandula stoechas* extract is a potent topical antioxidant that reduces oxidative stress and skin-damaging free radicals. Application of *Lavandula stoechas* extract has been shown to decrease lipoperoxidation, increase antioxidant enzyme activities, and decrease antioxidant enzyme activities.

*Rosmarinus officinalis* leaf extract is an extract from the leaf of *Rosmarinus officinalis*. *Rosmarinus officinalis* is native to the Mediterranean region, and is a woody, perennial herb with fragrant, evergreen, needle-like leaves and white, pink, purple, or blue flowers. It is a shrub that can reach up to 1.5 meters in height with leaves that are about 2 to 4 cm long with green (top surface) and white (bottom surface) coloring. In a preferred instance, the *Rosmarinus officinalis* leaf extract can be obtained from the leaf of *Rosmarinus officinalis*. The leaf can be subjected to a eutectigenesis extraction process using a fluid extraction mixture comprising betaine or hydrated betaine, a hydrogen bond donor compound (e.g., polyols, organic acids, etc.), and water. In particular, the leaf portion can be crushed or macerated and then subjected to the aforementioned eutectic fluid extraction mixture to obtain a eutectic extract. The eutectic extract can then be used in the compositions of the present invention. In some preferred instances, the hydrogen bond donor is an organic acid, preferably lactic acid. Eutectigenesis utilizes eutectic solvents which are mixtures of compounds having melting points lower than those of their constituents taken in isolation. In some instances, *Rosmarinus officinalis* is commercially available. In some instances, *Rosmarinus officinalis* can be supplied by Naturex (France) under the trade name ROSEMARY EUTECTYS BLA™. It was discovered in the context of the present invention that *Rosmarinus officinalis* leaf extract can reduce or inhibit contraction of myotubes by reducing or inhibiting an influx of calcium in the myotubes and reducing or preventing the occurrence of an action potential. It was also discovered that *Rosmarinus officinalis* leaf extract can inhibit or reduce MMP-1, MMP-3, and MMP-3 production or activity in skin cells (e.g., keratinocytes or human dermal fibroblasts). *Rosmarinus officinalis* (rosemary) leaf extract also exhibits antioxidant and anti-inflammatory activity. *Rosmarinus officinalis* (rosemary) leaf extract improves blood circulation and has some anti-bacterial activity. *Rosmarinus officinalis* (rosemary) leaf extract includes a number of aromatic components that provide a pleasant smell.

The extracts described herein can be extracts made through extraction methods known in the art and combinations thereof. Non-limiting examples of extraction methods include the use of liquid-liquid extraction, solid phase extraction, aqueous extraction, ethyl acetate, alcohol, acetone, oil, supercritical carbon dioxide, heat, pressure, pressure drop extraction, ultrasonic extraction, etc. Extracts can be a liquid, solid, dried liquid, re-suspended solid, etc. In certain instances, each of the extracts can be prepared by: (i) obtaining the desired plant part (e.g., leaf, stem, bark, flower, seed, etc.) or whole plant; (ii) crushing or macerating the plant part or whole plant; (iii) optionally drying the crushed or macerated plant part or whole plant; (iv) subjecting the crushed or macerated plant or plant part to an extraction solvent to a sufficient period of time (e.g., 1, 5, 10, 30, or 45 minutes or more, or 1, 6, 12, or 18 hours or more, or 2, 3, 4, 5, 6 days, or more) under room temperature (e.g., 20 to 30° C.) or heated (e.g., greater than 30° C. or more, preferably 30° C. to less than the boiling point of the solvent); (v) collecting the solution comprising the extracting solvent and the extracted plant material (e.g., liquid extract); and (vi) optionally removing the extracting solvent to obtain a dried plant extract; and (vii) optionally reconstituting the dried plant extract in a liquid carrier (e.g., water, alcohol, diol, etc.). It is also contemplated in the context of the present invention that plant material from *Rosmarinus officinalis* leaf, *Lavendula stoechas*, and/or the *Acmella oleracea* can be directly used without subjecting the plant material to an extraction technique.

C. Amounts of Ingredients

It is contemplated that the compositions of the present invention can include any amount of the ingredients discussed in this specification. The compositions can also include any number of combinations of additional ingredients described throughout this specification (e.g., pigments, or additional cosmetic or pharmaceutical ingredients). The concentrations of the ingredients within the compositions can vary. In non-limiting embodiments, for example, each of *Acmella oleracea* extract, *Lavandula stoechas* extract, and *Rosmarinus officinalis* (rosemary) leaf extract can independently comprise, consist essentially of, or consist of, in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the ingredients that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of ingredients in a given composition.

D. Vehicles

The compositions of the present invention can include or be incorporated into all types of vehicles and carriers. The vehicle or carrier can be a pharmaceutically or dermatologically acceptable vehicle or carrier. Non-limiting examples of vehicles or carriers include water, glycerin, alcohol, oil, a silicon containing compound, a silicone compound, and wax. Variations and other appropriate vehicles will be apparent to the skilled artisan and are appropriate for use in the present invention. In certain aspects, the concentrations and combinations of the compounds, ingredients, and agents can be selected in such a way that the combinations are chemically compatible and do not form complexes which precipitate from the finished product.

E. Structure

The compositions of the present invention can be structured or formulated into a variety of different forms. Non-limiting examples include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydro-alcoholic), anhydrous bases (such as lipsticks and powders), gels, masks, scrubs, body butters, peels, and ointments. Variations and other structures will be apparent to the skilled artisan and are appropriate for use in the present invention.

F. Additional Ingredients

In addition to the combination of ingredients disclosed by the inventors, the compositions can also include additional ingredients such as cosmetic ingredients and pharmaceutical active ingredients. Non-limiting examples of these additional ingredients are described in the following subsections.

1. Cosmetic Ingredients

The CTFA International Cosmetic Ingredient Dictionary and Handbook (2004 and 2008) describes a wide variety of non-limiting cosmetic ingredients that can be used in the context of the present invention. Examples of these ingredient classes include: fragrance agents (artificial and natural; e.g., gluconic acid, phenoxyethanol, and triethanolamine), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), flavoring agents/aroma agents (e.g., *Stevia rebaudiana* (sweetleaf) extract, and menthol), adsorbents, lubricants, solvents, moisturizers (including, e.g., emollients, humectants, film formers, occlusive agents, and agents that affect the natural moisturization mechanisms of the skin), water-repellants, UV absorbers (physical and chemical absorbers such as para-aminobenzoic acid ("PABA") and corresponding PABA derivatives, titanium dioxide, zinc oxide, etc.), essential oils, vitamins (e.g., B, D, E, and K), trace metals (e.g., zinc, calcium and selenium), anti-irritants (e.g., steroids and non-steroidal anti-inflammatories), botanical extracts (e.g., *Aloe vera*, chamomile, cucumber extract, *Ginkgo biloba, ginseng*, and rosemary), anti-microbial agents, antioxidants (e.g., BHT and tocopherol), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., sorbitol, urea, methyl gluceth-20, saccharide isomerate, and mannitol), exfoliants, waterproofing agents (e.g., magnesium/aluminum hydroxide stearate), skin conditioning agents (e.g., *aloe* extracts, allantoin, bisabolol, ceramides, dimethicone, hyaluronic acid, biosaccharide gum-1, ethylhexylglycerin, pentylene glycol, hydrogenated polydecene, octyldodecyl oleate, and dipotassium glycyrrhizate). Non-limiting examples of some of these ingredients are provided in the following subsections.

a. UV Absorption and/or Reflecting Agents

UV absorption and/or reflecting agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate (octinoxate), isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidene camphor, and isopentyl 4-methoxycinnamate. Non-limiting examples of physical sunblocks include, kaolin, talc, petrolatum and metal oxides (e.g., titanium dioxide and zinc oxide).

b. Moisturizing Agents

Non-limiting examples of moisturizing agents that can be used with the compositions of the present invention include amino acids, chondroitin sulfate, diglycerin, erythritol, fructose, glucose, glycerin, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrrolidone carboxylic acid, potassium PCA, propylene glycol, saccharide isomerate, sodium glucuronate, sodium PCA, sorbitol, sucrose, trehalose, urea, and xylitol.

Other examples include acetylated lanolin, acetylated lanolin alcohol, alanine, algae extract, *Aloe barbadensis, Aloe barbadensis* extract, *Aloe barbadensis* gel, *Althea officinalis* extract, apricot (*Prunus armeniaca*) kernel oil, arginine, arginine aspartate, *Arnica montana* extract, aspartic acid, avocado (*Persea gratissima*) oil, barrier sphingolipids, butyl alcohol, beeswax, behenyl alcohol, beta-sitosterol, birch (*Betula alba*) bark extract, borage (*Borago officinalis*) extract, butcherbroom (*Ruscus aculeatus*) extract, butylene glycol, *Calendula officinalis* extract, *Calendula officinalis* oil, candelilla (*Euphorbia* cerifera) wax, canola oil, caprylic/capric triglyceride, cardamom (*Elettaria cardamomum*) oil, carnauba (*Copernicia cerifera*) wax, carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dimethicone copolyol, dimethiconol, dioctyl adipate, dioctyl succinate, dipentaerythrityl hexacaprylate/hexacaprate, DNA, erythritol, ethoxydiglycol, ethyl linoleate, *Eucalyptus globulus* oil, evening primrose (*Oenothera biennis*) oil, fatty acids, *Geranium maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, *glycine*, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, *lavender* (*Lavandula angustifolia*) oil, lecithin, lemon (*Citrus medica limonum*) oil, linoleic acid, linolenic acid, *Macadamia ternifolia* nut oil, maltitol, *matricaria* (*Chamomilla recutita*) oil, methyl glucose sesquistearate, methylsilanol PCA, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*Mentha piperita*) oil, petrolatum, phospholipids, plankton extract, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, sandalwood (*Santalum album*) oil, serine, serum protein, sesame (*Sesamum indicum*) oil, shea butter (Butyrospermum parkii), silk powder, sodium chondroitin sulfate, sodium hyaluronate, sodium lactate, sodium palmitate, sodium PCA, sodium polyglutamate, soluble collagen, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang (*Cananga odorata*) oil.

c. Antioxidants

Additional antioxidants can be used in combination with *Lavandula stoechas* extract and *Rosmarinus officinalis* (rosemary) leaf extract. Non-limiting examples of antioxidants that can be used include acetyl cysteine, ascorbic acid derivatives like ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCI, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocophersolan, tocopheryl acetate, tocopheryl linoleate, tocopheryl nicotinate, tocopheryl succinate, and tris(nonylphenyl)phosphite.

d. Structuring Agents

In other non-limiting aspects, the compositions of the present invention can include a structuring agent. Structuring agents, in certain aspects, assist in providing rheological characteristics to the composition that contribute to stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

e. Emulsifiers

Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, cetearyl glucoside, cetearyl alcohol, C12-13 pareth-3, PPG-2 methyl glucose ether distearate, PPG-5-ceteth-20, bis-PEG/PPG-20/20 dimethicone, ceteth-10, polysorbate 80, cetyl phosphate, potassium cetyl phosphate, diethanolamine cetyl phosphate, polysorbate 60, glyceryl stearate, PEG-100 stearate, arachidyl alcohol, arachidyl glucoside, and mixtures thereof.

f. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In certain aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Michigan. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Michigan.

g. Exfoliating Agent

Exfoliating agents include ingredients that remove dead skin cells on the skin's outer surface. These agents may act through mechanical, chemical, and/or other means. Non-limiting examples of mechanical exfoliating agents include abrasives such as pumice, silica, cloth, paper, shells, beads, solid crystals, solid polymers, etc. Non-limiting examples of chemical exfoliating agents include acids and enzyme exfoliants. Acids that can be used as exfoliating agents include, but are not limited to, glycolic acid, lactic acid, citric acid, alpha hydroxy acids, beta hydroxy acids, etc. Other exfoliating agents known to those of skill in the art are also contemplated as being useful within the context of the present invention.

h. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 1600 to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, *macadamia* nut oil, tea tree oil, evening primrose oil, Spanish sage oil, Spanish rosemary oil, coriander oil, thyme oil, *pimento* berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, *geranium* oil, ginger oil, grapefruit oil, jasmine oil, juniper oil, *lavender* oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

i. Thickening Agents

Thickening agents, including thickener or gelling agents, include substances which that can increase the viscosity of a composition. Thickeners includes those that can increase the viscosity of a composition without substantially modifying the efficacy of the active ingredient within the composition. Thickeners can also increase the stability of the compositions of the present invention. In certain aspects of the present invention, thickeners include hydrogenated polyisobutene, trihydroxystearin, ammonium acryloyldimethyltaurate/vp copolymer, acrylates/C10-30 alkyl acrylate crosspolymer, or a mixture of them.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, Fourth edition, 1991, pp. 12 and 80). Examples of commercially available carboxylic acid polymers include carbomers, which are homopolymers of acrylic acid crosslinked with allyl ethers of sucrose or pentaerythritol (e.g., CARBOPOL™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three units.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and mixtures thereof.

j. Preservatives

Non-limiting examples of preservatives that can be used in the context of the present invention include quaternary ammonium preservatives such as polyquaternium-1 and benzalkonium halides (e.g., benzalkonium chloride ("BAC") and benzalkonium bromide), parabens (e.g., methylparabens and propylparabens), phenoxyethanol, benzyl alcohol, chlorobutanol, phenol, sorbic acid, thimerosal, or combinations thereof.

k. Emollients

Useful emollients include the following: (a) silicone oils and modifications thereof such as linear and cyclic polydimethylsiloxanes; amino, alkyl, alkylaryl, and aryl silicone oils; (b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride; (c) waxes such as carnauba, spermaceti, beeswax, lanolin, and derivatives thereof; (d) hydrophobic plant extracts; (e) hydrocarbons such as liquid paraffins, vaseline, microcrystalline wax, ceresin, squalene, pristan and mineral oil; (f) higher fatty acids such as lauric, myristic, palmitic, stearic, behenic, oleic, linoleic, linolenic, lanolic, isostearic, arachidonic and poly unsaturated fatty acids (PUFA); (g) higher alcohols such as lauryl, cetyl, stearyl, oleyl, behenyl, cholesterol and 2-hexydecanol alcohol; (h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; (i) essential oils and extracts thereof such as *mentha*, jasmine, camphor, white cedar, bitter orange peel, ryu, turpentine, cinnamon, bergamot, *citrus* unshiu, calamus, pine, *lavender*, bay, clove, hiba, *eucalyptus*, lemon, starflower, thyme, peppermint, rose, sage, sesame, ginger, basil, juniper, lemon grass, rosemary, rosewood, avocado, grape, grapeseed, myrrh, cucumber, watercress, *calendula*, elder flower, *geranium*, linden blossom, amaranth, seaweed, ginko, *ginseng*, carrot, guarana, tea tree, jojoba, comfrey, oatmeal, cocoa, neroli, vanilla, green tea, penny royal, *aloe* vera, menthol, cineole, eugenol, citral, citronelle, borneol, linalool, geraniol, evening primrose, camphor, thymol, spirantol, penene, limonene and terpenoid oils; (j) lipids such as cholesterol, ceramides, sucrose esters and pseudo-ceramides as described in European Patent Specification No. 556,957; (k) vitamins, minerals, and skin nutrients such as vitamins A, E, and K; vitamin alkyl esters, including vitamin C alkyl esters; magnesium, calcium, and milk; (1) sunscreens such as octyl methoxyl cinnamate (Parsol MCX) and butyl methoxy benzoylmethane (Parsol 1789); (1) phospholipids; (m) polyhydric alcohols such as glycerine and propylene glycol; and polyols such as polyethylene glycols; (n) anti-aging compounds such as alpha hydroxy acids, beta hydroxy acids; and (o) mixtures of any of the foregoing components, and the like.

k. Tackifiers

Examples of suitable tackifiers, include, but are not limited to, aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, hydrogenated rosin acids, hydrogenated rosin esters, polyisoprene, partially or fully hydrogenated polyisoprene, polybutenediene, partially or fully hydrogenated polybutenediene, and the like. As is evidenced by some of the cited examples, the tackifier may be fully or partially hydrogenated. The tackifier may also be non-polar. (Non-polar meaning that the tackifier is substantially free of monomers having polar groups. Preferably, the polar groups are not present, however, if they are present, they are preferably present in an amount of up to about 5% by weight, preferably up to about 2% by weight, and more preferably up to about 0.5% by weight.).

l. Colorant

The compositions of the present invention also contain at least one cosmetically acceptable colorant such as a pigment or dyestuff. Examples of suitable pigments include, but are not limited to, inorganic pigments, organic pigments, lakes, pearlescent pigments, iridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

n. Surfactant

Surfactants useful as the surfactant components in the compositions of the present invention include nonionic, anionic, cationic, and amphoteric (zwitterionic) surfactants and may be used in combination with each other.

o. pH Adjustors

The pH adjustors, include inorganic and organic acids and bases and in particular aqueous ammonia, citric acid, phosphoric acid, acetic acid, sodium hydroxide, lactic acid, levulinic acid, glycolic acid, tartaric acid, malic acid, pyrrolidonecarboxylic acid (PCA), succinic acid, citric acid, glutamic acid, 2-amino-2-methyl-1-propanol (AMP), and triethanolamine (TEA).

p. Reducing Agents

Suitable reducing agents include, but are not limited to, thiourea, salts (such as sodium salts) of thiosulfate, sulfite, bisulfite, metabisulfite, borohydride, and hypophosphite, ascorbic acid and salts, esters, and derivatives thereof (e.g., ascorbyl palmitate and ascorbyl polypeptide), and tocopherols and salts, esters, and derivatives thereof (e.g., tocopherol acetate). Other reducing agents are listed on pages 1655-56 of the INCI Handbook.

q. Fragrances

The compositions disclosed herein may optionally include a fragrance. Examples of possible fragrances include natural oils or naturally derived materials, and synthetic fragrances such as hydrocarbons, alcohols, aldehydes, ketones, esters, lactones, ethers, nitriles, and polyfunctionals. Non-limiting examples of natural oils include the following: basil (*Ocimum basilicum*) oil, bay (*Pimento acris*) oil, bee balm (*Monarda didyma*) oil, bergamot (*Citrus aurantium bergamia*) oil, cardamom (*Elettaria cardamomum*) oil, cedarwood (*Cedrus atlantica*) oil, chamomile (*Anthemis nobilis*) oil, cinnamon (*Cinnamomum cassia*) oil, citronella (*Cymbopogon nardus*) oil, clary (*Salvia sclarea*) oil, clove (*Eugenia caryophyllus*) oil, cloveleaf (*Eufenia caryophyllus*) oil, *Cyperus esculentus* oil, cypress (*Cupressus sempervirens*) oil, *Eucalyptus citriodora* oil, *geranium maculatum* oil, ginger (*Zingiber officinale*) oil, grapefruit (*Citrus grandis*) oil, hazel (*Corylus avellana*) nut oil, jasmine (*Jasminum officinale*) oil, *Juniperus communis* oil, *Juniperus* oxycedrus tar, *Juniperus virginiana* oil, kiwi (*Actinidia chinensis*) water, lavandin (*Lavandula hybrida*) oil, *lavender* (*Lavandula angustifolia*) oil, *lavender* (*Lavandula angustifolia*) water, lemon (*Citrus medica limonum*) oil, lemongrass (*Cymbopogon schoenanthus*) oil, lime (*Citrus aurantifolia*) oil, linden (*Tilia cordata*) oil, linden (*Tilia cordata*) water, mandarin orange (*Citrus nobilis*) oil, nutmeg (*Myristica fragrans*) oil, orange (*Citrus aurantium dulcis*) flower oil, orange (*Citrus aurantium dulcis*) oil, orange (*Citrus aurantium dulcis*) water, patchouli (*Pogostemon cablin*) oil, peppermint (*Menthe piperita*) oil, peppermint (*Menthe peperita*) water, rosemary (*Rosmarinus officinalis*) oil, rose oil, rose (*Rosa damascena*) extract, rose (*Rosa multiflora*) extract, rosewood (*Aniba rosaeodora*) extract, sage (*Salvia officinalis*) oil, sandalwood (*Santalum album*) oil, spearmint (*Menthe viridis*) oil, tea tree (*Melaleuca alternifolia*) oil, menthol, and ylang ylang (*Cananga odorata*) oil. Some non-limiting examples of synthetic hydrocarbon fragrances include caryophyllene, β-farnesene, limonene, α-pinene, and, β-pinene. Some non-limiting examples of synthetic alcohol fragrances include bacdanol, citronellol, linalool, phenethyl alcohol, and α-terpineol (R═H). Some non-limiting examples of synthetic aldehyde fragrances include 2-methyl undecanal, citral, hexyl cinnamic aldehyde, isocycolcitral, lilial, and 10-undecenal. Some non-limiting examples of synthetic ketone fragrances include cashmeran, α-ionone, isocyclemone E, koavone, muscone, and tonalide. Some non-limiting examples of synthetic ester fragrances include benzyl acetate, 4-t-butylcyclohexyl acetate (cis and trans), cedryl acetate, cyclacet, isobornyl acetate, and α-terpinyl acetate (R=acetyl). Some non-limiting examples of synthetic lactone fragrances include coumarin, jasmine lactone, muskalactone, and peach aldehyde. Some non-limiting examples of synthetic ether fragrances include ambroxan, anther, and galaxolide. Some non-limiting examples of synthetic nitrile fragrances include cinnamonitrile and gernonitrile. Finally, some non-limiting examples of synthetic polyfunctional fragrances include amyl salicylate, isoeugenol, hedione, heliotropine, lyral, and vanillin.

r. Foaming Agents

The foaming agents include, for example, sodium lauryl sulfate, sodium lauroyl sarcosine, sodium alkyl sulfosuccinates, sodium coconut oil fatty acid monoglycerol sulfonates, sodium α-olefin sulfonates, N-acylamino acid salts such as N-acyl glutamate, 2-alkyl-N-carboxymethyl-N-hydroxyethylimidazolinium betaine, maltitol fatty acid esters, sucrose fatty acid esters, polyglycerol fatty acid esters, fatty acid diethanolamides, polyoxyethylene sorbitan monostearate, polyoxyethylene hydrogenated castor oil and polyoxyethylene fatty acid esters. These foaming agents are usable either alone or in combination of two or more of them.

s. Tanning Agents

Suitable tanning agents include, without limitation, alpha-hydroxy aldehydes and ketones, glyceraldehyde and related alcohol aldehydes, various indoles, imidazoles and derivatives thereof, and various approved pigmentation agents. Other suitable tanning agents include, without limitation, methyl glyoxal, glycerol aldehyde, erythrulose, alloxan, 2,3-dihydroxysuccindialdehyde, 2,3-dimethoxysuccindialdehyde, 2-amino-3-hydroxy-succindialdehyde and 2-benzylamino-3-hydroxysuccindialdehyde.

t. Astringents

Suitable astringents include, without limitation, aluminum citrate, aluminum lactate, extracts of birch, extracts of coffee, extracts of evening primrose, extracts of grape, extracts of henna, extracts of ivy, extracts of lemon, extracts of witch hazel, Ammonium and Potassium Alum, Aluminum Triphosphate, Aluminum Glycinate and Aluminum Phenolsulfate, Alcloxa, Aldioxa, Aluminum Stearate, Aluminum Sulfate and Aluminum Citrate, Sodium Aluminum Phosphate, Sodium Alum, Sodium Aluminum Chlorohydroxy Lactate, Calcium Lactate, Calcium Chloride, Calcium Sulfate Hydrate, Sodium Aluminum Lactate, Zinc Acetate, Zinc Chloride, Zinc Sulfate, Zinc Lactate, Zinc Zeolite, Zinc Phenolsulfonate, and combinations thereof. What is meant by an extract is either the whole fruit, bean, and/or plant or select constituents of such fruit, bean, and/or plant.

u. Antiseptics

Suitable antiseptics include, without limitation, methyl, ethyl, propyl, or butyl ester of p-oxybenzoic acid, phenoxyethanol, o-phenylphenol, dehydroacetic acid, or salts thereof, p-cresol, m-cresol, o-chlor-m-xylenol, peppermint oil, *Echinacea*, bloodroot, cayenne, tea tree oil, wild bergamont, chaparral, stinging metal, bay, myrrh, rhatany bark, toothache tree, *calendula*, chamomile, mupirocin, neomycin sulfate, bacitracin, polymyxin B, 1-ofloxacin, tetracyclines (chlortetracycline hydrochloride, oxytetracycline hydrochloride and tetrachcycline hydrochoride), clindamycin phsphate, gentamicin sulfate, benzalkonium chloride, benzethonium chloride, hexylresorcinol, methylbenzethonium chloride, phenol, quaternary ammonium compounds, triclocarbon, triclosan, and tea tree oil.

v. Deodorants and Antiperspirants

Suitable antiperspirants and deodorants include, without limitation, zinc salts such as zinc sulfate and zinc chloride, glycinates such as aluminum zirconium glycinate, aluminum chlorohydrate, aluminum zirconium tetrachlorohydrex, zinc carbonate, orthophenylphenol, and quaternary ammonium compounds such as dimethyl benzyl ammonium chloride and hexamethonium chloride.

w. Lighteners

Examples of skin lighteners include, without limitation, hydroquinone, kojic acid, licorice and/or its derivatives, ascorbic acid and/or its derivatives, arbutin, bearberry extract, *Glycyrrhiza glabra* and its derivatives, *Chlorella vulgaris* extract, *perilla* extract, coconut fruit extract, and/or other depigmenting agents.

x. Biocides

Examples of biocides include, without limitation, triclosan, 3,4,4'-trichlorocarbanilide (triclocarban); 3,4,4'-trifluoromethyl-4,4'-dichlorocarbanilide (cloflucarban); 5-chloro-2-methyl-4-isothiazolin-3-one; iodopropynlbutylcarbamate; 8-hydroxyquinoline; 8-hydroxyquinoline citrate; 8-hydroxyquinoline sulfate; 4-chloro-3,5-xylenol(chloroxylenol); 2-bromo-2-nitropropane-1,3-diol; diazolidinyl urea; butoconazole; nystatin; terconazole; nitrofurantoin; phenazopyridine; acyclovir; clortrimazole; chloroxylenol; chlorhexidine; miconazole; terconazole; butylparaben; ethylparaben; methylparaben; methylchloroisothiazoline; methylisothiazoline; a mixture of 1,3-bis(hydroxymethyl)-5,5-dimethylhydantoin and 3-iodo-2-propynyl butyl carbamate; oxyquinoline; EDTA; tetrasodium EDTA; p-hydroxyl benzoic acid ester; alkyl pyridinum compounds; coco phosphatidyl PG-dimonium chloride; chlorhexidine gluconate; chlorhexidine digluconate; chlorhexidine acetate; chlorhexidine isethionate; chlorhexidine hydrochloride; benzalkonium chloride; benzethonium chloride; polyhexamethylene biguanide; and mixtures thereof.

2. Pharmaceutical Ingredients

Pharmaceutical active agents are also contemplated as being useful with the compositions of the present invention. Non-limiting examples of pharmaceutical active agents include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, anti-seborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, photosensitizing actives, skin protectant/barrier agents, steroids including hormones and corticosteroids, sunburn treatment agents, sunscreens, transdermal actives, wart treatment agents, wound treatment agents, wound healing agents, etc.

G. Kits

Kits are also contemplated as being used in certain aspects of the present invention. For instance, compositions of the present invention can be included in a kit. A kit can include a container. Containers can include an ampoule, a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of the composition. In other embodiments, the container can be squeezed (e.g., metal, laminate, or plastic tube) to dispense a desired amount of the composition. The composition can be dispensed as a spray, an aerosol, a liquid, a fluid, or a semi-solid. The containers can have spray, pump, or squeeze mechanisms. A kit can also include instructions for employing the kit components as well the use of any other compositions included in the container. Instructions can include an explanation of how to apply, use, and maintain the compositions.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Collagen is one of the primary components of connective tissue and helps keep skin looking young. Collagen is the most abundant protein in the human body, accounting for about a third of its protein composition. When collagen levels are high, skin is firmer, smoother, and more supple. Human collagen production starts to decline after the age of twenty at which point collagen production slows at a rate of about one percent per year, the skin gradually becomes thinner and more fragile. As age increases, fine lines begin to form around the mouth and eyes, and forehead wrinkles begin to deepen.

Example 1

Example Formulation

Table 1 represents a skin lotion formulation of the present invention, which is structured as an oil-in-water emulsion.

TABLE 1*

| Ingredient | % Concentration (by weight) |
|---|---|
| Water | 44.4 |
| Alcohol | 9.2 |
| Dimethyl isosorbide | 8.0 |
| Cetyl esters | 5.0 |
| Pentylene glycol | 5.0 |
| Neopentyl glycol diheptanoate | 4.0 |
| Stearyl alcohol | 3.0 |
| Caprylic/capric triglyceride | 2.9 |
| Ethoxydiglycol | 2.5 |
| Propylene glycol | 2.5 |
| Cetearyl olivate | 2.1 |
| *Mangifera indica* (mango) seed butter | 2.0 |
| Sorbitan olivate | 1.9 |
| Propanediol | 1.7 |
| Lactic acid | 1.2 |
| Triethanolamine | 1.2 |
| Betaine | 1.0 |
| Acrylates/C10-30 alkyl acrylate crosspolymer | 0.6 |
| Cetyl palmitate | 0.6 |
| Sorbitan palmitate | 0.5 |
| Xanthan gum | 0.3 |
| *Acmella oleracea* extract | 0.21 |
| *Lavandula stoechas* extract | 0.12 |
| *Rosmarinus officinalis* (rosemary) leaf extract | 0.06 |
| Disodium EDTA | 0.05 |
| Menthol | 0.05 |

*Formulation can be prepared by mixing the ingredients in a beaker at room temperature or under heat, such as at 70-75° C., until homogenous. Subsequently, the formulation can be cooled to standing room temperature (20-25° C.). Further, and if desired, additional ingredients can be added, for example, to modify the rheological properties of the composition or ingredients that provide benefits to skin. Excipients can be added, for example, to modify the rheological properties of the composition. Alternatively, the amount of water can be varied so long as the amount of water in the composition is at least 5% w/w, and preferably between 10 to 40% w/w.

Example 2

In Vitro Myotube Contraction Data

Each of *Rosmarinus officinalis* leaf extract, *Lavendula stoechas* extract, and *Acmella oleracea* extract were found to reduce contraction of myotubes, which can result in reduced muscle contraction of a facial muscle and reduced appearance of facial deep lines or wrinkles and dynamic facial wrinkles and forehead wrinkles that are caused due to repetitive facial muscle contraction. The methodology used to obtain the data included: (1) Primary Human Skeletal muscle myoblasts (HSMM) were made to differentiate into Myotubes; (2) Myotubes were then treated with 'inducers' (Acetcholine), which in turn causes an influx of calcium and creating an action potential; and (3) This action potential causes the muscle cells to contract. The concentration amounts of each extract used and the resulting effect on inhibition of calcium levels are provided in Table 2.

TABLE 2

| Ingredient | Inhibition of Calcium Levels |
|---|---|
| *Rosmarinus Officinalis* Leaf extract* | 1.0 wt. % conc. = 100% inhibition |
| | 2.0 wt. % conc. = 100% inhibition |
| *Lavendula Stoechas* Extract** | 0.5% wt. conc. = 30% inhibition |
| | 1.0% wt. conc. = 30% inhibition |
| *Acmella Oleracea* Extract*** | 0.5% wt. conc. = 77% inhibition |
| | 1.0% wt. conc. = 96% inhibition |

**Rosmarinus officinalis* leaf extract was a eutectic extract in which the solvent used to prepare the extract was a fluid mixture of betaine, lactic acid, and water. The extract was supplied by Naturex (France) under the trade name Rosemary EUTECTYS BLA ™.

***Lavendula stoechas* extract used was a supercritical $CO_2$ extract of the flower/leaf/stem of *Lavendula stoechas*. The $CO_2$ extract was mixed with caprylic/capric triglycerides. The extract was supplied by Barnet Products LLC (Englewood Cliffs, New Jersey (USA)) under the trade name Stochey's.

****Acmella oleracea* extract used was a hydro-ethanolic extract in which the solvent included a fluid mixture of water, ethanol, and 1,3 propanediol. The ethanol was removed from the resulting extraction fluid. The extract was supplied by Gattefossé (France) under the trade name Gatuline ® Expression AF.

Example 3

In Vitro Myotube Contraction Data

*Acmella oleracea* extract was found to increase collagen production in human dermal fibroblasts. The data and amount of extract used is provided in Table 3.

TABLE 3

| Ingredient | Increased Collagen Production |
|---|---|
| *Acmella Oleracea* Extract* | 1.0 wt. % conc. = 61% increased collagen production |

**Acmella oleracea* extract used was a hydro-ethanolic extract in which the solvent included a fluid mixture of water, ethanol, and 1,3 propanediol. The ethanol was removed from the resulting extraction fluid. The extract was supplied by Gattefossé (France) under the trade name Gatuline ® Expression AF.

Collagen is an extracellular matrix protein critical for skin structure. Increased synthesis of collagen helps improve skin firmness and elasticity. This bioassay was used to examine the effect of *Acmella oleracea* extract on the production of procollagen peptide (a precursor to collagen) by human dermal fibroblasts. The endpoint of this assay was a spectrophotometric measurement that reflected the presence of procollagen peptide and cellular viability. The assay employed the quantitative sandwich enzyme immunoassay technique whereby a monoclonal antibody specific for procollagen peptide was pre-coated onto a microplate. Standards and samples were pipetted into the wells and any procollagen peptide present was bound by the immobilized antibody. After washing away any unbound substances, an enzyme-linked polyclonal antibody specific for procollagen peptide was added to the wells. Following a wash to remove any unbound antibody-enzyme reagent, a substrate solution was added to the wells and color developed in proportion to the amount of procollagen peptide bound in the initial step. Color development was stopped and the intensity of the color at 450 nm was measured using a microplate reader.

For generation of samples and controls, subconfluent normal human adult dermal fibroblasts (Cascade Biologics) were cultivated in standard DMEM growth medium with 10% fetal bovine serum (Mediatech) at 37° C. in 10% CO2. The cells were treated with each of the tested ingredients and controls for 3 days. Following incubation, cell culture medium was collected and the amount of procollagen peptide secretion was quantified using the sandwich enzyme linked immuno-sorbant assay (ELISA) from Takara (#MK101) as explained above.

Example 4

In Vitro Laminin Expression Data

*Acmella oleracea* extract was found to increase laminin production in human dermal fibroblasts. The data and amount of extract used is provided in Table 4.

TABLE 4

| Ingredient | Increased Laminin Production |
|---|---|
| *Acmella Oleracea* Extract* | 1.0 wt. % conc. = 53% increased laminin production |

**Acmella oleracea* extract used was a hydro-ethanolic extract in which the solvent included a fluid mixture of water, ethanol, and 1,3 propanediol. The ethanol was removed from the resulting extraction fluid. The extract was supplied by Gattefossé (France) under the trade name GATULINE ® EXPRESSION AF.

Laminin is a major protein in the dermal-epidermal junction (DEJ) (also referred to as the basement membrane). The DEJ is located between the dermis and the epidermis and interlocks forming fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Laminin is a structural glycoproteins located in the DEJ. Considered a glue that holds the cells together, laminin is secreted by dermal fibroblasts to help facilitate intra- and inter-cellular adhesion of the epidermal cells to the DEJ. Laminin secretion was monitored by quantifying laminin in cell supernatants of cultured human fibroblasts treated for 3 days with culture medium with the test ingredient (*Acmella oleracea* extract). Following incubation, laminin was measured using immunofluorescent antibodies directed against each protein in an enzyme linked immuno-sorbant assay (ELISA). Measurements were normalized for cellular metabolic activity, as determined by bioconversion of 3-(4,5-dimethylthiazol-2-yl)-5-(3-carboxymethoxyphenyl)-2-(4-sulfophenyl)-2H-tetrazolium (MTS).

Example 5

In Vitro MMP Inhibition Data

*Rosmarinus officinalis* leaf extract was found to inhibit matrix metalloproteinases (MMP) 1, 3, and 9 in human dermal fibroblasts. The data and amount of extract used is provided in Table 5.

TABLE 5

| Ingredient | Inhibition of MMP-1, 3, and 9 Production |
|---|---|
| *Rosmarinus Officinalis* Leaf extract* | MMP-1 @ 1.0 wt. % conc. = −98% inhibition<br>MMP-3 @ 1.0 wt. % conc. = −39% inhibition |

**Rosmarinus officinalis* leaf extract was a eutectic extract in which the solvent used to prepare the extract was a fluid mixture of betaine, lactic acid, and water. The extract was supplied by Naturex (France) under the trade name ROSEMARY EUTECTYS BLA ™.

Matrix Metalloproteinase 1 Enzyme Activity (MMP-1) Assay: MMPs are extracellular proteases that play a role in many normal and disease states by virtue of their broad substrate specificity. MMP-1 substrates include collagen IV. The Molecular Probes Enz/Chek Gelatinase/Collagenase Assay kit (#E12055) utilizes a fluorogenic gelatin substrate to detect MMP1 protease activity. Upon proteolytic cleavage, bright green fluorescence is revealed and may be monitored using a fluorescent microplate reader to measure enzymatic activity. The Enz/Chek Gelatinase/Collagenase Assay kit (#E12055) from Invitrogen is designed as an in vitro assay to measure MMP-1 enzymatic activity. The *Rosmarinus officinalis* leaf extract was assayed. The assay relies upon the ability of purified MMP-1 enzyme to degrade a fluorogenic gelatin substrate. Once the substrate is specifically cleaved by MMP-1 bright green fluorescence is revealed and was monitored using a fluorescent microplate reader. *Rosmarinus officinalis* leaf extract was incubated in the presence or absence of the purified enzyme and substrate to determine their protease inhibitor capacity.

Matrix Metalloproteinase 3 and 9 Enzyme Activity (MMP-3 and MMP-9) Assay: MMP-3 substrates include collagens, fibronectins, and laminin; while MMP-9 substrates include collagen VII, fibronectins and laminin. Using Colorimetric Drug Discovery kits from BioMol International for MMP3 (AK-400) and MMP-9 (AK-410), this assay was designed to measure protease activity of MMPs using a thiopeptide as a chromogenic substrate (Ac-PLG-[2-mercapto-4-methyl-pentanoyl]-LG-OC2H5)5,6. The MMP cleavage site peptide bond is replaced by a thioester bond in the thiopeptide. Hydrolysis of this bond by an MMP produces a sulfhydryl group, which reacts with DTNB [5,5'-dithiobis(2-nitrobenzoic acid), Ellman's reagent] to form 2-nitro-5-thiobenzoic acid, which can be detected by its absorbance at 412 nm (ε=13,600 M-lcm-1 at pH 6.0 and above 7). The *Rosmarinus officinalis* leaf extract was assayed.

Example 6

In Vivo Clinical Data

In vivo clinical data on the combination of *Rosmarinus officinalis* leaf extract, *Lavendula stoechas* extract, and *Acmella oleracea* extract was obtained. The *Rosmarinus officinalis* leaf extract was a eutectic extract in which the solvent used to prepare the extract was a fluid mixture of betaine, lactic acid, and water. The extract was supplied by Naturex (France) under the trade name ROSEMARY EUTECTYS BLA™. The *Lavendula stoechas* extract used was a supercritical $CO_2$ extract of the flower/leaf/stem of *Lavendula stoechas*. The $CO_2$ extract was mixed with caprylic/capric triglycerides. The extract was supplied by Barnet Products LLC (Englewood Cliffs, New Jersey (USA)) under the trade name STOCHEY'S. The *Acmella oleracea* extract used was a hydro-ethanolic extract in which the solvent included a fluid mixture of water, ethanol, and 1,3 propanediol. The ethanol was removed from the resulting extraction fluid. The extract was supplied by Gattefossé (France) under the trade name GATULINE® EXPRESSION AF.

The purpose of the in vivo clinical study was to evaluate the efficacy of a combination of the three extracts for muscle relaxation and wrinkle reduction over four weeks of twice-daily application on 30 individuals (n=30). The combination of the three extracts was placed in a dermatologically acceptable vehicle. The dermatologically acceptable vehicle was designed to test the efficacy of the combination of the three extracts. The other ingredients in the dermatologically acceptable vehicle were not believed to contribute to the clinical data results in either a positive or negative manner. The amounts of each extract used in the dermatologically acceptable vehicle was *Rosmarinus officinalis* leaf extract at 1 wt. %, *Lavendula stoechas* extract at 2 wt. %, and *Acmella oleracea* extract at 2 wt. %.

The in vivo clinical study design was a randomized controlled, investigator-blinded clinical study. The following parameters were used: (1) subjects-females between the ages of 35 and 70 in good general health (no physical required) and were clinically determined to have scored 3-7 (inclusively) on a 10-point scale for moderate frown/glabellar lines; (2) test site—*glabella* area; (3) evaluation time points-baseline (week 0), week 2, week 4, and week 8; (4) testing method-electromyography (EMG) for muscle response (mV/s): AUC (area under the curve); and (5) clinical endpoints measured-fine lines and wrinkles and skin texture on a 0 to 9 scale.

Figure 2:
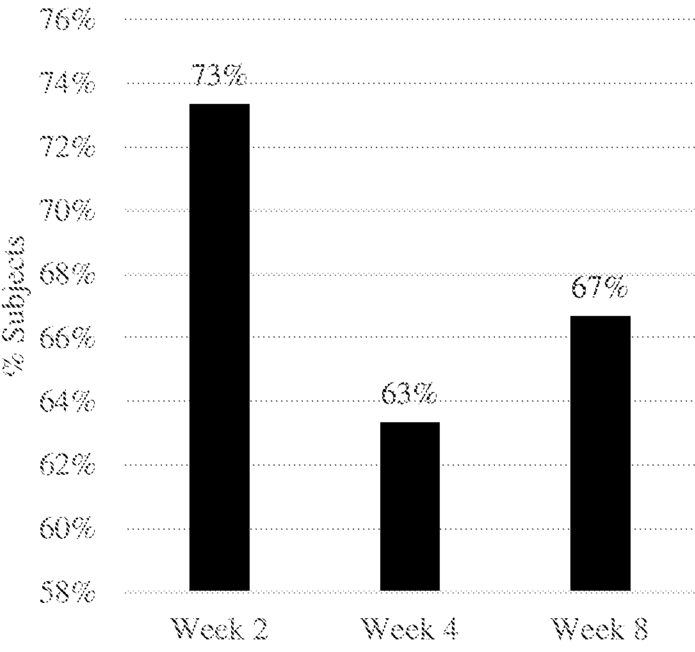
FIG. 2 provides data illustrating the % of people showing improvement from baseline (0 week) in the EMG response area (mV.s) for muscle contraction in the *glabella* region for a group of people using a composition of the present invention having a combination of *Rosmarinus officinalis* leaf extract, *Lavendula stoechas* extract, and *Acmella oleracea* extract. The % of people showing improvement illustrates reduced muscle contraction in the *glabella* region over time (2 weeks, 4 weeks, and 8 weeks).
Figure 3:
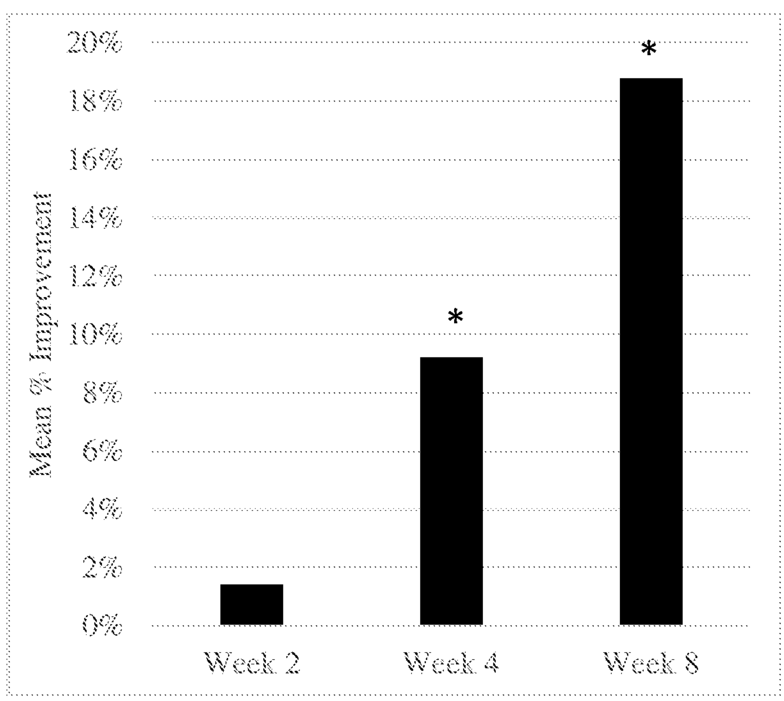
FIG. 3 provides data illustrating the mean % of improvement from baseline (0 week) for reduced appearance of fine lines and wrinkles for a group of people using a composition of the present invention having a combination of *Rosmarinus officinalis* leaf extract, *Lavendula stoechas* extract, and *Acmella oleracea* extract. The mean % of improvement illustrates reduced appearance of fine lines and wrinkles in the treated area over time (2 weeks, 4 weeks, and 8 weeks). "*" indicates $p<0.05$ statistically significant improvement when compared to baseline (0 weeks).
Figure 4:
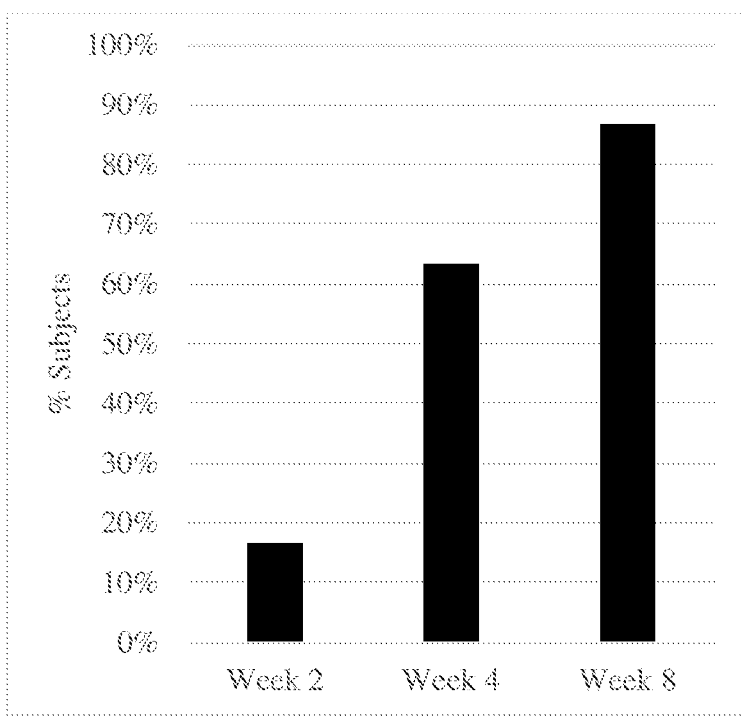
FIG. 4 provides data illustrating the % of people showing improvement from baseline (0 week) in the reduction of fine lines and wrinkles for a group of people using a composition of the present invention having a combination of *Rosmarinus officinalis* leaf extract, *Lavendula stoechas* extract, and *Acmella oleracea* extract. The % of people showing improvement illustrates reduced appearance of fine lines and wrinkles in the treated area over time (2 weeks, 4 weeks, and 8 weeks).

FIGS. 1-2 provide data illustrating muscle contraction inhibition via EMG testing. FIGS. 3-4 provide data illustrating reduction in the appearance of fine lines and wrinkles. As illustrated in these FIGS. 1-4, the data suggests that the combination of *Rosmarinus officinalis* leaf extract, *Lavendula stoechas* extract, and *Acmella oleracea* extract can reduce facial muscle contraction and can reduce the overall appearance of fine lines and wrinkles. The following Table 6 provides data illustrating the EMG response and clinical comparison between a well-known injectable neuromodulator (Botox® (onabotulinumtoxinA)) and the combination of *Rosmarinus officinalis* leaf extract, *Lavendula stoechas* extract, and *Acmella oleracea* extract.

TABLE 6

| | % EMG Response (AUC) | | % Clinical Improvement of Wrinkles | |
|---|---|---|---|---|
| | BoTox - 5 U (n = 5)** | Combination of three extracts (n = 30) | BoTox - 5 U (n = 5)** | Combination of three extracts (n = 30) |
| Week 2 | 58%* | 11% | 31%* | 1% |
| Week 4 | 40%* | 10% | 35%* | 9%* |
| Week 8 | Not measured | 16%* | Not measured | 19%* |

*p < 0.05 statistically significant improvement when compared to baseline.

**The BoTox - 5 U study was used as a control to validate the method and performed on 5 individuals. Each individual was administered 5 units (U) of Botox to the glabella region and % EMG Response (AUC) was measured. This was done to standardize the aforementioned combination of extracts study.

Example 7

In Vivo Clinical Data

In a comparative clinical study, additional in vivo clinical data on the combination of *Rosmarinus officinalis* leaf extract, *Lavendula stoechas* extract, and *Acmella oleracea* extract was obtained. The *Rosmarinus officinalis* leaf extract was a eutectic extract in which the solvent used to prepare the extract was a fluid mixture of betaine, lactic acid, and water. The extract was supplied by Naturex (France) under the trade name ROSEMARY EUTECTYS BLA™. The *Lavendula stoechas* extract used was a supercritical $CO_2$ extract of the flower/leaf/stem of *Lavendula stoechas*. The $CO_2$ extract was mixed with caprylic/capric triglycerides. The extract was supplied by Barnet Products LLC (Englewood Cliffs, New Jersey (USA)) under the trade name STOCHEY'S. The *Acmella oleracea* extract used was a hydro-ethanolic extract in which the solvent included a fluid mixture of water, ethanol, and 1,3 propanediol. The ethanol was removed from the resulting extraction fluid. The extract was supplied by Gattefossé (France) under the trade name GATULINE® EXPRESSION AF.

The purpose of the comparative in vivo clinical study was to evaluate the efficacy of a combination of the three extracts for muscle relaxation and wrinkle reduction over four weeks of twice-daily application on Experimental Group 1 participants using a micro-roller (n=33) versus application on Experimental Group 2 participants without using a micro-roller (n=30). The combination of the three extracts was placed in a dermatologically acceptable vehicle as the test product. The dermatologically acceptable vehicle was designed to test the efficacy of the combination of the three extracts when applied with a micro-roller versus application without a micro-roller. Study participants in Experimental Group 1 used a 1.0 mm microroller. Study participants applied the composition containing the three extracts between their eyebrows in the morning and the evening after cleansing their face with a personal cleanser. For Experimental Group 1, study participants used the micro-roller 3 times per week in the evenings by rolling the micro-roller back and forth 4 to 5 times between eyebrows changing directions with each pass. For both Experimental Group 1 and Experimental Group 2, an occlusive patch (e.g., SCARAWAY®) was placed between eyebrows overnight. The other ingredients in the dermatologically acceptable vehicle were not believed to contribute to the clinical data results in either a positive or negative manner. The amounts of each extract used in the dermatologically acceptable vehicle was *Rosmarinus officinalis* leaf extract at 1 wt. %, *Lavendula stoechas* extract at 2 wt. %, and *Acmella oleracea* extract at 2 wt. %.

The comparative in vivo clinical study design was a randomized controlled, investigator-blinded clinical study. The following parameters were used: (1) subjects—females between the ages of 35 and 70 in good general health (no physical required) and were clinically determined to have scored 3-7 (inclusively) on a 10-point scale for moderate frown/glabellar lines; (2) test site—*glabella* area; (3) test product—*Frontalis*; supplemental products—SCARA-WAY® occlusive patch, and microroller; (4) evaluation time points—baseline (week 0), week 2, week 4, and week 8; (5) testing method-electromyography (EMG) for muscle response (mV/s):AUC (area under the curve); and (6) clinical endpoints measured—fine lines and wrinkles and skin texture on a 0 to 9 scale.

that application of the composition containing the combination of *Rosmarinus officinalis* leaf extract, *Lavendula stoechas* extract, and *Acmella oleracea* extract, combined with using a micro-roller to promote penetration of the composition into the skin, can significantly improve skin texture and roughness in the glabellar area after 2, 4, and 8 weeks. It was determined that 79% of subjects showed improvement in skin smoothness after 8 weeks after application of the composition with a micro-roller. It was further determined that application of the composition without a micro-roller was still effective at improving skin smoothness after 8 weeks.

The following Table 7 provides data illustrating the EMG response and clinical comparison between a well-known injectable neuromodulator (Botox® (onabotulinumtoxinA)) and the combination of *Rosmarinus officinalis* leaf extract, *Lavendula stoechas* extract, and *Acmella oleracea* extract applied with a micro-roller and applied without a micro-roller.

TABLE 7

| | % EMG Response (AUC) | | | % Clinical Improvement of Wrinkles | | |
|---|---|---|---|---|---|---|
| | BoTox - 5 U (n = 5)** | Experimental Group 1 (w/ micro-roller) (n = 33) | Experimental Group 2 (w/o micro-roller) (n = 30) | BoTox - 5 U (n = 5)** | Experimental Group 1 (w/ micro-roller) (n = 33) | Experimental Group 2 (w/o micro-roller) (n = 30) |
| Week 2 | 58%* | 16%* | 11% | 31%* | 3% | 1% |
| Week 4 | 40%* | 16%* | 10% | 35%* | 9%* | 9%* |
| Week 8 | Not measured | 21%* | 16%* | Not measured | 18%* | 19%* |

*$p < 0.05$ statistically significant improvement when compared to baseline.

**The BoTox - 5 U study was used as a positive control in comparing Experimental Group 1 and Experimental Group 2 and was performed on 5 individuals. Each individual was administered 5 units (U) of Botox to the glabella region and % EMG Response (AUC) was measured. This was done to standardize the aforementioned combination of extracts study.

Figure 5:
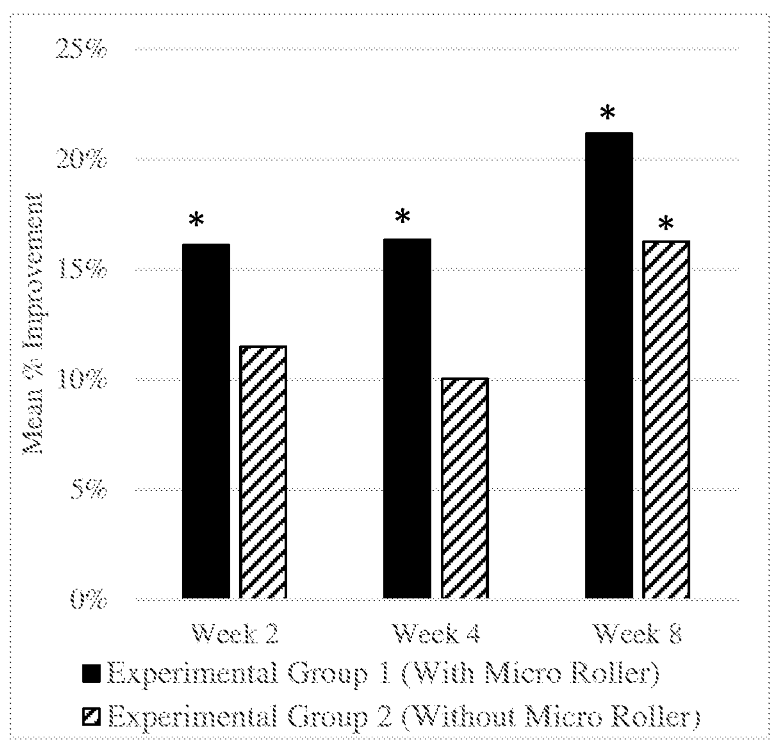
FIG. 5 provides data illustrating the mean % of improvement from baseline (0 week) in the EMG response area (mV.s) for muscle contraction in the *glabella* region for a group of people using a composition of the present invention having a combination of *Rosmarinus officinalis* leaf extract, *Lavendula stoechas* extract, and *Acmella oleracea* extract, and applying the composition with a micro-roller versus applying the composition without a micro-roller. The mean % of improvement illustrates a faster and stronger reduction in facial muscle contraction at 2, 4, and 8 weeks compared to baseline when using a micro-roller with application of the composition. "*" indicates $p<0.05$ statistically significant improvement when compared to baseline (0 weeks).
Figure 6:
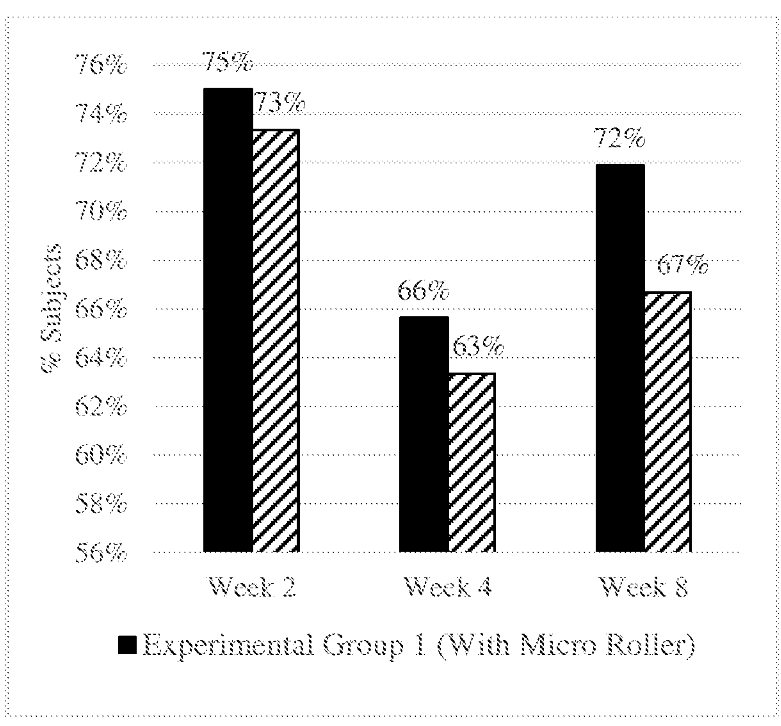
FIG. 6 provides data illustrating the % of people showing improvement from baseline (0 week) in the EMG response area (mV.s) for muscle contraction in the *glabella* region for a group of people using a composition of the present invention having a combination of *Rosmarinus officinalis* leaf extract, *Lavendula stoechas* extract, and *Acmella oleracea* extract. The % of people showing improvement illustrates a faster and stronger reduction in facial muscle contraction at 2, 4, and 8 weeks in the *glabella* region when using a micro-roller with application of the composition.
Figure 7:
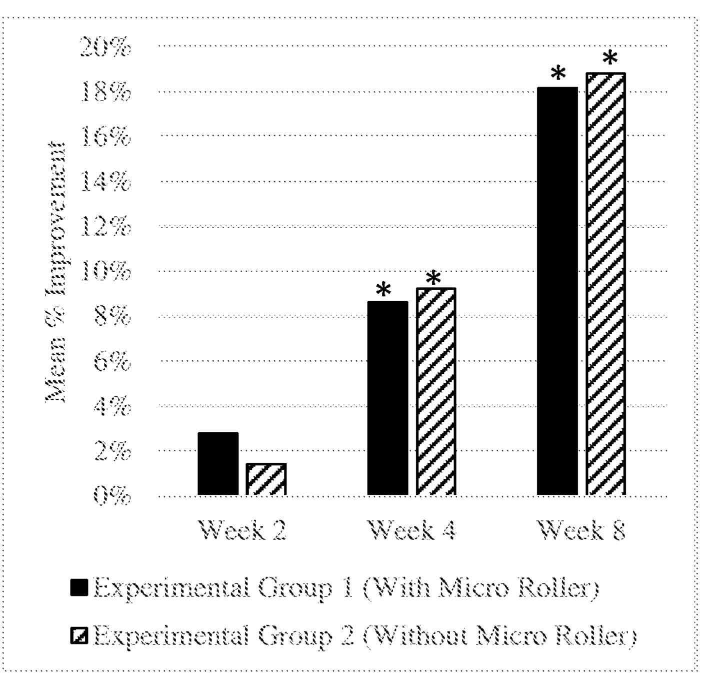
FIG. 7 provides data illustrating the mean % of improvement from baseline (0 week) for reduced appearance of fine lines and wrinkles for a group of people using a composition of the present invention having a combination of *Rosmarinus officinalis* leaf extract, *Lavendula stoechas* extract, and *Acmella oleracea* extract. The mean % of improvement illustrates reduced appearance of fine lines and wrinkles in the treated area over time (2 weeks, 4 weeks, and 8 weeks) when using a micro-roller with application of the composition and without using a micro-roller with application of the composition. "*" indicates $p<0.05$ statistically significant improvement when compared to baseline (0 weeks).
Figure 8:
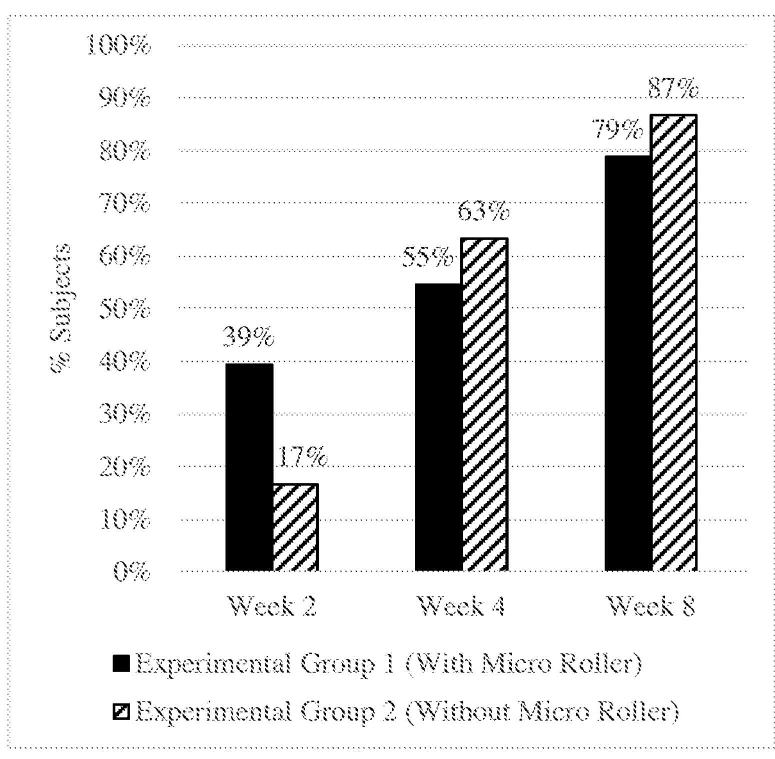
FIG. 8 provides data illustrating the % of people showing improvement from baseline (0 week) in the reduction of fine lines and wrinkles for a group of people using a composition of the present invention having a combination of *Rosmarinus officinalis* leaf extract, *Lavendula stoechas* extract, and *Acmella oleracea* extract. The % of people showing improvement illustrates reduced appearance of fine lines and wrinkles in the treated area over time (2 weeks, 4 weeks, and 8 weeks) when using a micro-roller with application of the composition and without using a micro-roller with application of the composition.

FIGS. 5-6 provide data illustrating muscle contraction inhibition via EMG testing comparing percent improvement between application with a micro-roller and application without a micro-roller. FIGS. 7-8 provide data illustrating reduction in the appearance of fine lines and wrinkles comparing percent improvement between application with a micro-roller and application without a micro-roller. As illustrated in FIGS. 5-8, the data suggests that application of the composition containing the combination of *Rosmarinus officinalis* leaf extract, *Lavendula stoechas* extract, and *Acmella oleracea* extract, combined with using a micro-roller to promote penetration of the composition into the skin, can reduce facial muscle contraction and can reduce the overall appearance of fine lines and wrinkles. It was determined that application of the composition with a micro-roller was effective at attaining a faster and stronger reduction in facial muscle contraction at 2, 4, and 8 weeks compared to baseline, and reduced fine lines and wrinkles and skin texture within 4 weeks, where 79% of subjects showed improvement in both fine lines and wrinkles and skin smoothness after 8 weeks. It was further determined that application of the composition without a micro-roller was still effective at attaining a reduction in facial muscle contraction after 8 weeks, and reduced fine lines and wrinkles and skin texture within 4 weeks, where 87% of subjects showed improvement in both fine lines and wrinkles and 90% in skin smoothness after 8 weeks.

Figure 9:
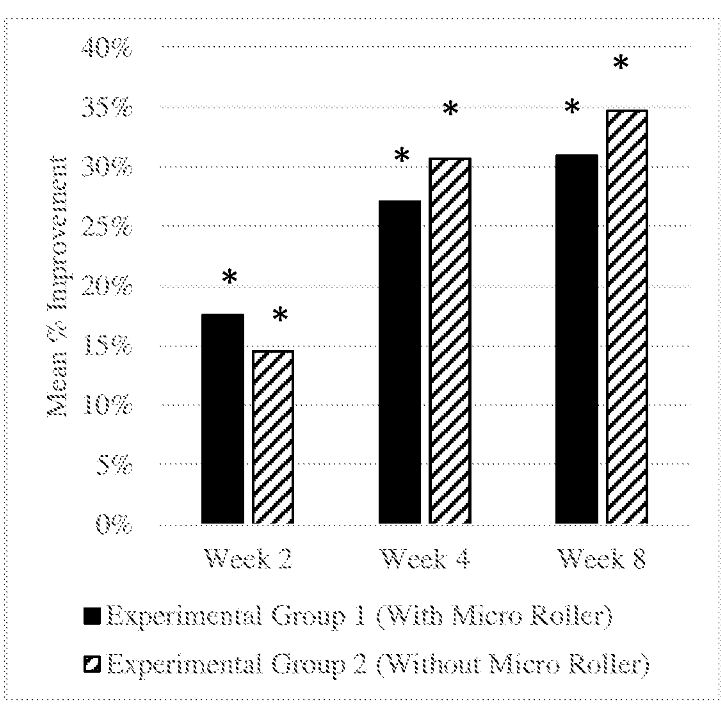
FIG. 9 provides data illustrating the mean % of improvement from baseline (0 week) for skin texture/roughness for a group of people using a composition of the present invention having a combination of *Rosmarinus officinalis* leaf extract, *Lavendula stoechas* extract, and *Acmella oleracea* extract. The mean % of improvement illustrates improved skin texture/roughness in the treated area over time (2 weeks, 4 weeks, and 8 weeks) when using a micro-roller with application of the composition and without using a micro-roller with application of the composition. "*" indicates $p<0.05$ statistically significant improvement when compared to baseline (0 weeks).
Figure 10:
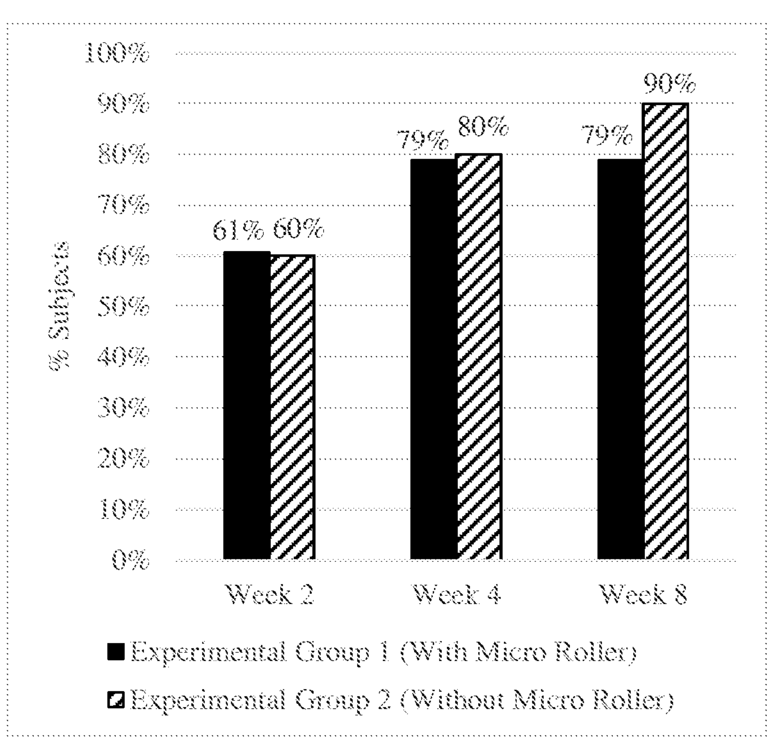
FIG. 10 provides data illustrating the % of people showing improvement from baseline (0 week) in skin texture/roughness for a group of people using a composition of the present invention having a combination of *Rosmarinus officinalis* leaf extract, *Lavendula stoechas* extract, and *Acmella oleracea* extract. The % of people showing improvement illustrates improved skin texture/roughness in the treated area over time (2 weeks, 4 weeks, and 8 weeks) when using a micro-roller with application of the composition and without using a micro-roller with application of the composition.

FIGS. 9-10 provide data illustrating improvement in skin texture/roughness comparing percent improvement between application with a micro-roller and application without a micro-roller. As illustrated in FIGS. 9-10, the data suggests

Example 8

Additional Assays

Additional assays that can be used to determine the efficacy of any one of the ingredients or any combination of ingredients or compositions having said combination of ingredients disclosed throughout the specification and claims can be determined by methods known to those of ordinary skill in the art. The following are non-limiting assays that can be used in the context of the present invention. It should be recognized that other testing procedures can be used, including, for example, objective and subjective procedures.

Elastin Stimulation Assay: Elastin is a connective tissue protein that helps skin resume shape after stretching or contracting. Elastin is also an important load-bearing protein used in places where mechanical energy is required to be stored. Elastin is made by linking many soluble tropoelastin protein molecules, in a reaction catalyzed by lysyl oxidase. Elastin secretion and elastin fibers may be monitored in cultured human fibroblasts by a direct ELISA sandwich method and analyzed using the Meso Scale Discovery system SECTOR 2400 Imaging system.

Laminin and Fibronectin Stimulation Assay: Laminin and fibronectin are major proteins in the dermal-epidermal junction (DEJ) (also referred to as the basement membrane). The DEJ is located between the dermis and the epidermis interlocks forming fingerlike projections called rete ridges. The cells of the epidermis receive their nutrients from the blood vessels in the dermis. The rete ridges increase the surface area of the epidermis that is exposed to these blood vessels and the needed nutrients. The DEJ provides adhesion of the two tissue compartments and governs the structural integrity of the skin. Laminin and fibronectin are two structural glycoproteins located in the DEJ. Considered the glue that holds the cells together, laminin and fibronectin are secreted by dermal fibroblasts to help facilitate intra- and inter-cellular adhesion of the epidermal calls to the DEJ.

Laminin and fibronectin secretion may be monitored by quantifying laminin and fibronectin in cell supernatants of cultured human fibroblasts treated for 3 days with culture medium with or without 1.0% final concentration of the test ingredient(s). Following incubation, laminin and fibronectin content may be measured using immunofluorescent antibodies directed against each protein in an enzyme linked immuno-sorbant assay (ELISA).

ORAC Assay: Oxygen Radical Absorption (or Absorbance) Capacity (ORAC) of any one of the active ingredients, combination of ingredients, or compositions having said combinations disclosed in the specification can also be assayed by measuring the antioxidant activity of such ingredients or compositions. Antioxidant activity indicates a capability to reduce oxidizing agents (oxidants). This assay quantifies the degree and length of time it takes to inhibit the action of an oxidizing agent, such as oxygen radicals, that are known to cause damage to cells (e.g., skin cells). The ORAC value of any one of the active ingredients, combination of ingredients, or compositions having said combinations disclosed in the specification can be determined by methods known to those of ordinary skill in the art (see U.S. Publication Nos. 2004/0109905 and 2005/0163880; and commercially available kits such as Zen-Bio ORAC Antioxidant Assay kit (#AOX-2)). The Zen-Bio ORAC Antioxidant Assay kit measures the loss of fluorescein fluorescence over time due to the peroxyl-radical formation by the breakdown of AAPH (2,2'-axobis-2-methyl propanimidamide, dihydrochloride). Trolox, a water soluble vitamin E analog, serves as positive control inhibition fluorescein decay in a dose dependent manner.

Matrix Metalloproteinase 1 Enzyme Activity (MMP1) Assay: An in vitro matrix metalloprotease (MMP) inhibition assay. MMPs are extracellular proteases that play a role in many normal and disease states by virtue of their broad substrate specificity. MMP1 substrates include collagen IV. The Molecular Probes Enz/Chek Gelatinase/Collagenase Assay kit (#E12055) utilizes a fluorogenic gelatin substrate to detect MMP1 protease activity. Upon proteolytic cleavage, bright green fluorescence is revealed and may be monitored using a fluorescent microplate reader to measure enzymatic activity.

The Enz/Chek Gelatinase/Collagenase Assay kit (#E12055) from Invitrogen is designed as an in vitro assay to measure MMP1 enzymatic activity. The active ingredients, any one of the combination of ingredients, or compositions having said combinations disclosed in the specification can be assayed. The assay relies upon the ability of purified MMP1 enzyme to degrade a fluorogenic gelatin substrate. Once the substrate is specifically cleaved by MMP1 bright green fluorescence is revealed and may be monitored using a fluorescent microplate reader. Test materials are incubated in the presence or absence of the purified enzyme and substrate to determine their protease inhibitor capacity.

Cyclooxygenase (COX) Assay: An in vitro cyclooxygenase-1 and -2 (COX-1, -2) inhibition assay. COX is a bifunctional enzyme exhibiting both cyclooxygenase and peroxidase activities. The cyclooxygenase activity converts arachidonic acid to a hydroperoxy endoperoxide (Prostaglandin G2; PGG2) and the peroxidase component reduces the endoperoxide (Prostaglandin H2; PGH2) to the corresponding alcohol, the precursor of prostaglandins, thromboxanes, and prostacyclins. This COX Inhibitor screening assay measures the peroxidase component of cyclooxygenases. The peroxidase activity is assayed colorimetrically by monitoring the appearance of oxidized N,N,N',N'-tetramethyl-p-phenylenediamine (TMPD). This inhibitor screening assay includes both COX-1 and COX-2 enzymes in order to screen isozyme-specific inhibitors. The Colormetric COX (ovine) Inhibitor screening assay (#760111, Cayman Chemical) can be used to analyze the effects of each of the active ingredients, any one of the combination of ingredients, or compositions having said combinations disclosed in the specification on the activity of purified cyclooxygnase enzyme (COX-1 or COX-2). According to manufacturer instructions, purified enzyme, heme and test extracts can be mixed in assay buffer and incubated with shaking for 15 min at room temperature. Following incubation, arachidonic acid and colorimetric substrate can be added to initiate the reaction. Color progression can be evaluated by colorimetric plate reading at 590 nm. The percent inhibition of COX-1 or COX-2 activity can be calculated compared to non-treated controls to determine the ability of test extracts to inhibit the activity of purified enzyme.

Lipoxygenase (LO) Assay: An in vitro lipoxygenase (LO) inhibition assay. LOs are non-heme iron-containing dioxygenases that catalyze the addition of molecular oxygen to fatty acids. Linoleate and arachidonate are the main substrates for LOs in plants and animals. Arachadonic acid may then be converted to hydroxyeicosotrienenoic (HETE) acid derivatives that are subsequently converted to leukotrienes, potent inflammatory mediators. This assay provides an accurate and convenient method for screening lipoxygenase inhibitors by measuring the hydroperoxides generated from the incubation of a lipoxygenase (5-, 12-, or 15-LO) with arachidonic acid. The Colorimetric LO Inhibitor screening kit (#760700, Cayman Chemical) can be used to determine the ability of each of the active ingredients, any one of the combination of ingredients, or compositions having said combinations disclosed in the specification to inhibit enzyme activity. Purified 15-lipoxygenase and test ingredients can be mixed in assay buffer and incubated with shaking for 10 min at room temperature. Following incubation, arachidonic acid can be added to initiate the reaction and the mixtures can be incubated for an additional 10 min at room temperature. Colorimetric substrate can be added to terminate catalysis and color progression can be evaluated by fluorescence plate reading at 490 nm. The percent inhibition of lipoxyganse activity can be calculated compared to non-treated controls to determine the ability of each of the active ingredients, any one of the combination of ingredients, or compositions having said combinations disclosed in the specification to inhibit the activity of purified enzyme.

Elastase Assay: ENZCHEK® Elastase Assay (Kit #E-12056) from Molecular Probes (Eugene, Oregon USA) can be used as an in vitro enzyme inhibition assay for measuring inhibition of elastase activity for each of the active ingredients, any one of the combination of ingredients, or compositions having said combinations disclosed in the specification. The EnzChek kit contains soluble bovine neck ligament elastin that can be labeled with dye such that the conjugate's fluorescence can be quenched. The non-fluorescent substrate can be digested by elastase or other proteases to yield highly fluorescent fragments. The resulting increase in fluorescence can be monitored with a fluorescence microplate reader. Digestion products from the elastin substrate have absorption maxima at ~505 nm and fluorescence emission maxima at ~515 nm. The peptide, N-methoxysuccinyl-Ala-Ala-Pro-Val-chloromethyl ketone, can be used as a selective, collective inhibitor of elastase when utilizing the EnzChek Elastase Assay Kit for screening for elastase inhibitors.

Oil Control Assay: An assay to measure reduction of sebum secretion from sebaceous glands and/or reduction of sebum production from sebaceous glands can be assayed by using standard techniques known to those having ordinary skill in the art. In one instance, the forehead can be used. Each of the active ingredients, any one of the combination of ingredients, or compositions having said combinations disclosed in the specification can be applied to one portion of the forehead once or twice daily for a set period of days (e.g., 1, 2, 3, 4, 5, 6, 7, 8, 9, 10, 11, 12, 13, 14, or more days), while another portion of the forehead is not treated with the composition. After the set period of days expires, then sebum secretion can be assayed by application of fine blotting paper to the treated and untreated forehead skin. This is done by first removing any sebum from the treated and untreated areas with moist and dry cloths. Blotting paper can then be applied to the treated and untreated areas of the forehead, and an elastic band can be placed around the forehead to gently press the blotting paper onto the skin. After 2 hours the blotting papers can be removed, allowed to dry and then transilluminated. Darker blotting paper correlates with more sebum secretion (or lighter blotting paper correlates with reduced sebum secretion.

Erythema Assay: An assay to measure the reduction of skin redness can be evaluated using a Minolta Chromometer. Skin erythema may be induced by applying a 0.2% solution of sodium dodecyl sulfate on the forearm of a subject. The area is protected by an occlusive patch for 24 hrs. After 24 hrs, the patch is removed and the irritation-induced redness can be assessed using the a* values of the Minolta Chroma Meter. The a* value measures changes in skin color in the red region. Immediately after reading, the area is treated with the active ingredients, any one of the combination of ingredients, or compositions having said combinations disclosed in the specification. Repeat measurements can be taken at regular intervals to determine the formula's ability to reduce redness and irritation.

Skin Moisture/Hydration Assay: Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance. Each of the active ingredients, any one of the combination of ingredients, or compositions having said combinations disclosed in the specification can be assayed according to this process.

Skin Clarity and Reduction in Freckles and Age Spots Assay: Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether each of the active ingredients, any one of the combination of ingredients, or compositions having said combinations disclosed in the specification is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as (a2+b2)½.

Skin Dryness, Surface Fine Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Clinical Grading of Skin Tone Assay: Clinical grading of skin tone can be performed via a ten point analog numerical scale: (10) even skin of uniform, pinkish brown color. No dark, erythremic, or scaly patches upon examination with a hand held magnifying lens. Microtexture of the skin very uniform upon touch; (7) even skin tone observed without magnification. No scaly areas, but slight discolorations either due to pigmentation or erythema. No discolorations more than 1 cm in diameter; (4) both skin discoloration and uneven texture easily noticeable. Slight scaliness. Skin rough to the touch in some areas; and (1) uneven skin coloration and texture. Numerous areas of scaliness and discoloration, either hypopigmented, erythremic or dark spots. Large areas of uneven color more than 1 cm in diameter. Evaluations may be independently made by two clinicians and averaged.

Clinical Grading of Skin Smoothness Assay: Clinical grading of skin smoothness can be analyzed via a ten point analog numerical scale: (10) smooth, skin is moist and glistening, no resistance upon dragging finger across surface; (7) somewhat smooth, slight resistance; (4) rough, visibly altered, friction upon rubbing; and (1) rough, flaky, uneven surface. Evaluations may be independently made by two clinicians and averaged.

Skin Smoothness and Wrinkle Reduction Assay With Methods Disclosed in Packman et al. (1978): Skin smoothness and wrinkle reduction can also be assessed visually by using the methods disclosed in Packman et al. (1978). For example, at each subject visit, the depth, shallowness and the total number of superficial facial lines (SFLs) of each subject can be carefully scored and recorded. A numerical score can be obtained by multiplying a number factor times a depth/width/length factor. Scores are obtained for the eye area and mouth area (left and right sides) and added together as the total wrinkle score.

Skin Firmness Assay with a Hargens Ballistometer: Skin firmness can be measured using a Hargens ballistometer, a device that evaluates the elasticity and firmness of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer: Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Appearance of Lines and Wrinkles Assay with Replicas: The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subject's face and analyzing the replicas image using a computer image analysis system. Replicas can be taken from the eye area and the neck area, and photographed with a digital camera using a low angle incidence lighting. The digital images can be analyzed with an image processing program.

Surface Contour of the Skin Assay with a Profilometer/Stylus Method: The surface contour of the skin can be measured by using the profilometer/stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fixed axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt is the maximum vertical distance between the highest peak and lowest trough, and Rz is the mean peak amplitude minus the mean peak height. Values are given as a calibrated value in mm. Equipment should be standardized prior to each use by scanning metal standards of know values. Ra Value can be computed by the following equation: Ra=Standardize roughness; lm=the traverse (scan) length; and y=the absolute value of the location of the profile relative to the mean profile height (x-axis).

MELANODERM™ Assay: In other non-limiting aspects, the efficacy of each of the active ingredients, any one of the combination of ingredients, or compositions having said combinations disclosed in the specification can be evaluated by using a skin analog, such as, for example, MELANODERM™. Melanocytes, one of the cells in the skin analog, stain positively when exposed to L-dihydroxyphenyl alanine (L-DOPA), a precursor of melanin. The skin analog, MELANODERM™, can be treated with a variety of bases containing each of the active ingredients, any one of the combination of ingredients, or compositions having said combinations disclosed in the specification or with the base alone as a control. Alternatively, an untreated sample of the skin analog can be used as a control.

Production of Filaggrin: Changes in the production of filaggrin in keratinocytes due to each of the active ingredients, any one of the combination of ingredients, or compositions having said combinations disclosed in the specification can be measured. Filaggrin is the precursor to Natural Moisturizing Factor (NMF) in the skin. Increased NMF increases the moisture content of the skin. Filaggrin production in treated and non-treated keratinocytes can be determined using a bioassay that analyzes filaggrin concentration in keratinocyte cell lysates. A non-limiting example of a bioassay that can be used to quantify filaggrin production is the PROTEINSIMPLE® SIMON™ western blotting protocol. For each sample, normal human epidermal keratinocytes (NHEK) are grown in EPI-200-Mattek EPILIFE® growth media with calcium from Life Technologies (M-EP-500-CA). NHEK are incubated in growth medium overnight at 37° C. in 5% $CO_2$ prior to treatment. NHEK are then incubated in growth medium with 1% test compound/extract or no compound/extract (negative control) for 24 to 36 hours. The NHEK can then be washed, collected, and stored on ice or colder until lysed on ice using a lysis buffer and sonication. The protein concentrations of the samples can be determined and used to normalize the samples. The lysates can be stored at −80° C. until use in the quantification assay.

The PROTEINSIMPLE® SIMON™ western blotting bioassay assay employs a quantitative western blotting immunoassay technique using an antibody specific for filaggrin to quantitatively detect filaggrin in the test samples. Cell samples are lysed and normalized for protein concentration. Normalized samples and molecular weight standards can then be loaded and ran on a denatured protein separation gel using capillary electrophoresis. The proteins in the gel are immobilized and immunoprobed using a primary antibody specific for filaggrin. The immobilized proteins can then be immunoprobed with an enzyme-linked detection antibody that binds the primary antibody. A chemiluminescent substrate solution can then be added to the immobilized proteins to allow chemiluminescent development in proportion to the amount of filaggrin bound in the immobilization. The chemiluminescent development is stopped at a specific time and the intensity of the chemiluminescent signal can be measured and compared to positive and negative controls.

Production of Occludin: Changes in the production of occludin in keratinocytes due to each of the active ingredients, any one of the combination of ingredients, or compositions having said combinations disclosed in the specification can be measured. Occludin is a protein critical to the formulation of tight junctions and the skin's moisture barrier function. A non-limiting example of how occludin production in treated and non-treated keratinocytes can be determined is by the use of a bioassay that analyzes occludin concentration in keratinocyte cell lysates. The bioassay can be performed using PROTEINSIMPLE® SIMON™ western blotting protocol. For the samples, adult human epidermal keratinocytes (HEKa) from Life Technologies (C-005-5C) can be grown at 37° C. and 5% $CO_2$ for 24 hours in Epilife growth media with calcium from Life Technologies (M-EP-500-CA) supplemented with Keratinocyte Growth Supplement (HKGS) from Life Technologies (S-101-5). HEKa are then incubated in growth medium with test compound/extract, no compound/extract for negative control, or with 1 mM $CaCl_2$) for positive control for 24 to 48 hours. The HEKa are then washed, collected, and stored on ice or colder until lysed on ice using a lysis buffer and sonication. The protein concentrations of the samples can be determined and used to normalize the samples. The lysates are stored at −80° C. until use in the bioassay.

The PROTEINSIMPLE® SIMON™ western blotting bioassay assay employs a quantitative western blotting immunoassay technique using an antibody specific for occludin to quantitatively detect occludin in the test samples. Cell samples are lysed and normalized for protein concentration. Normalized samples and molecular weight standards are then loaded and ran on a denatured protein separation gel using capillary electrophoresis. The proteins in the gel are then immobilized and immunoprobed using a primary antibody specific for occludin. The immobilized proteins are immunoprobed with an enzyme-linked detection antibody that binds the primary antibody. A chemiluminescent substrate solution is then added to the immobilized proteins to allow chemiluminescent development in proportion to the amount of occludin bound in the immobilization. The chemiluminescent development can be stopped at a specific time and the intensity of the chemiluminescent signal can be measured and compared to positive and negative controls.

Keratinocyte Monolayer Permeability: Changes in the permeability of a keratinocyte monolayer due to each of the active ingredients, any one of the combination of ingredients, or compositions having said combinations disclosed in the specification can be measured. Keratinocyte monolayer permeability is a measure of skin barrier integrity. Keratinocyte monolayer permeability in treated and non-treated keratinocytes can be determined using, as a non-limiting example, the In Vitro Vascular Permeability assay by Millipore (ECM642). This assay analyzes endothelial cell adsorption, transport, and permeability. Briefly, adult human epidermal keratinocytes from Life Technologies (C-005-5C) can be seeded onto a porous collagen-coated membrane within a collection well. The keratinocytes are then incubated for 24 hours at 37° C. and 5% $CO_2$ in Epilife growth media with calcium from Life Technologies (M-EP-500-CA) supplemented with Keratinocyte Growth Supplement (HKGS) from Life Technologies (S-101-5). This incubation time allows the cells to form a monolayer and occlude the membrane pores. The media is then replaced with fresh media with (test sample) or without (non-treated control) test compounds/extracts and the keratinocytes are incubated for an additional 48 hours at 37° C. and 5% $CO_2$. To determine permeability of the keratinocyte monolayer after incubation with/without the test compound/extract, the media is replaced with fresh media containing a high molecular weight Fluorescein isothiocyanate (FITC)-Dextran and the keratinocytes are incubated for 4 hours at 37° C. and 5% $CO_2$. During the 4 hours incubation, FITC can pass through the keratinocytes monolayer and porous membrane into the collection well at a rate proportional to the monolayer's permeability. After the 4 hour incubation, cell viability and the content of FITC in the collection wells can be determined. For the FITC content, the media in the collection well is collected and fluorescence of the media determined at 480 nm (Em) when excited at 520 nm. Percent permeability and percent change in comparison to the non-treated controls can be determined by the following equations: Percent Permeability=((Mean Ex/Em of test sample)/Mean Ex/Em untreated control)*100; Percent Change=Percent Permeability of test sample—Percent Permeability of untreated control.

Production of Hyaluronic Acid: Changes in the production of hyaluronic acid in human dermal fibroblasts due to each of the active ingredients, any one of the combination of ingredients, or compositions having said combinations disclosed in the specification can be measured. HA is a polysaccharide involved in stabilization of the structure of the matrix and is involved in providing turgor pressure to tissue and cells. As one non-limiting example, HA production in treated and non-treated adult human dermal fibroblasts (HDFa) cells can be determined using the Hyaluronan DuoSet ELISA kit from R&D Systems (DY3614). In this assay, for production of samples, subconfluent HDFa cells from Cascade Biologics (C-13-5C) are incubated at 37° C. and 10% $CO_2$ in starvation medium (0.15% fetal bovine serum and 1% Penicillin Streptomycin solution in Dulbecco's Modified Eagle Medium) for 72 hours prior to treatment. The cells are then incubated with fresh starvation medium with either test compound, positive control (phorbol 12-myristate 13-acetate from Sigma-Aldrich (P1585) and platelet derived growth factor from Sigma-Aldrich (P3201)), or no additive for 24 hours. Media is then collected and frozen at −80° C. until use in the ELISA assay.

Briefly, the ELISA assay employs a quantitative sandwich enzyme immunoassay technique whereby a capture antibody specific for HA can be pre-coated onto a microplate. Standards and media from treated and untreated cells are pipetted into the microplate wells to enable any HA present to be bound by the immobilized antibody. After washing away any unbound substances, an enzyme-linked detection antibody specific for HA is added to the wells. Following a wash to remove any unbound antibody-enzyme reagent, a substrate solution is added to the wells to allow color development in proportion to the amount of HA bound in the initial step. The color development is stopped at a specific time and the intensity of the color at 450 nm can be measured using a microplate reader.

Inhibition of Hyaluronidase Activity: Changes in the activity of hyaluronidase due to each of the active ingredients, any one of the combination of ingredients, or compositions having said combinations disclosed in the specification can be measured. Hyaluronidase is an enzyme that degrades HA. HA is a polysaccharide involved in stabilization of the structure of the matrix and is involved in providing turgor pressure to tissue and cells. As one non-limiting example, hyaluronidase activity can be determined using an in vitro protocol modified from Sigma-Aldrich protocol #EC 3.2.1.35. Briefly, hyaluronidase type 1-S from Sigma-Aldrich (H3506) is added to microplate reaction wells containing test compound or controls. Tannic acid can be used as a positive control inhibitor, no test compound can be added for the control enzyme, and wells with test compound or positive control but without hyaluronidase can be used as a background negative control. The wells are incubated at 37° C. for 10 minutes before addition of substrate (HA). Substrate is added and the reactions incubated at 37° C. for 45 minutes. A portion of each reaction solution is then transferred to and gently mixed in a solution of sodium acetate and acetic acid pH 3.75 to stop that portion of the reaction (stopped wells). The stopped wells and the reaction wells should both contain the same volume of solution after addition of the portion of the reaction solution to the stopped wells. Both the reaction wells and the stopped wells are incubated for 10 minutes at room temperature. Absorbance at 600 nm is then measured for both the reaction wells and the stopped wells. Inhibition can be calculated using the following formulas: Inhibitor (or control) activity=(Inhibitor stopped wells absorbance at 600 nm—inhibitor reaction wells absorbance at 600 nm); Initial activity=control enzyme absorbance at 600 nm; Percent Inhibition=[(Initial activity/Inhibitor Activity)*100]-100.

Peroxisome Proliferator-Activated Receptor Gamma (PPAR-γ) Activity: Changes in the activity of PPAR-γ due to each of the active ingredients, any one of the combination of ingredients, or compositions having said combinations disclosed in the specification can be measured. PPAR-γ is a receptor critical for the production of sebum. As one non-limiting example, the activity of PPAR-γ can be determined using a bioassay that analyzes the ability of a test compound or composition to inhibit binding of a ligand. Briefly, fluorescent small-molecule pan-PPAR ligand, FLUORMONE™ Pan-PPAR Green, available from Life Technologies (PV4894), can be used to determine if test compounds or compositions are able to inhibit binding of the ligand to PPAR-7. The samples wells include PPAR-γ and fluorescent ligand and either: test compound or composition (test); a reference inhibitor, rosiglitazone (positive control); or no test compound (negative control). The wells are incubated for a set period of time to allow the ligand opportunity to bind the PPAR-7. The fluorescence polarization of each sample well can then be measured and compared to the negative control well to determine the percentage of inhibition by the test compound or composition.

Cytokine array: Human epidermal keratinocytes are cultured to 70-80% confluency. The media in the plate is aspirated and 0.025% trypsin/EDTA is added. When the cells are rounded, the culture dish is gently tapped to release the cells. The trypsin/EDTA containing cells are removed from the culture dish and neutralized. Cells are centrifuged for 5 min. at 180× g to form a pellet of cells. The supernatant is aspirated. The resulting pellet is resuspended in EPILIFE™ media (Cascade Biologics). The cells are seeded in 6-well plates at approximately 10-20% confluency. After the cells are approximately 80% confluent, the media is aspirated and 1.0 ml of EPILIFE™, along with phorbol 13-Myristate 12-acetate ("PMA") (a known inducer of inflammation) and the test composition dilutions are added to two replicate wells (i.e., 1.0% (100 μl of 100× stock) and 0.1% (10 μl of 100× stock) test compositions are diluted into a final volume of 1 ml EpiLife Growth Medium). The media is gently swirled to ensure adequate mixing. In addition, 1.0 ml of EPILIFE™ is added to the control wells, with and without additional PMA. The plates are then incubated at 37±1° C. and 5.0±1% $CO_2$ for approximately 5 hours after dosing. Following this 5-hour incubation, all media is collected in conical tubes and frozen at −70° C.

For analysis, a 16-pad hybridization chamber is attached to 16-pad FAST slides arrayed in triplicate with 16 anti-cytokine antibodies plus experimental controls (Whatman BioSciences), and the slides are placed into a FASTFrame (4 slides per frame) for processing. Arrays are blocked for 15 min. at room temperature using 70 ml S&S Protein Array Blocking buffer (Whatman Schleicher and Scheull). Blocking buffer is removed and 70 ml of each supernatant sample is added to each array. Arrays are incubated for 3 hours at room temperature with gentle agitation. Arrays are washed 3 times with TBS-T. Arrays are treated with 70 ml of an antibody cocktail, containing one biotinylated antibody corresponding to each of the arrayed capture antibodies. Arrays are incubated for 1 hour at room temperature with gentle agitation. Arrays are washed 3 times with TBS-T. Arrays are incubated with 70 ml of a solution containing streptavidin-Cy5 conjugate for 1 hour at room temperature with gentle agitation. Arrays are washed 3 times with TBS-T, quickly rinsed in de-ionized water, and dried.

Slides can be imaged in a Perkin-Elmer ScanArray 4000 confocal fluorescent imaging system. Array images can be saved and analyzed using Imaging Research ArrayVision software. Briefly, spot intensities are determined by subtracting background signal. Spot replicates from each sample condition can be averaged and then compared to the appropriate controls.

Endothelial Tube Formation: Endothelial tube formation is involved in angiogenesis and micro-vessel capillary formation. Capillary formation and angiogenesis may contribute to redness and rosacea of the skin. The ability for endothelial cells to form tubes in the presence or absence of test extracts and compounds may be determined using a capillary tubule disruption assay with pre-formed primary human umbilical vein endothelial cells (HUVEC) in a cell culture system.

Briefly, HUVECs are cultured in vitro on Extracellular Matrix, which stimulates the attachment and tubular morphogenesis of endothelial cells to form capillary-like lumen structures. These in vitro formed capillary tubules are similar to human blood vessel capillaries in many aspects. The capillary tube assay is based on this phenomenon and is used for evaluation of potential vasculature targeting agents.

HUVEC cultures are grown in a 5% $CO_2$ 37° C. cell incubator. The full growth medium for HUVECs is Endothelial Cell Basal Medium (EBM) supplemented with 2% fetal bovine serum (FBS), 12 μg/ml bovine brain extract, 1 μg/ml hydrocortisone, and 1 μg/ml GA-1000 (gentamicin-amphothericin). HUVEC cultures between passage 3 and 8 may be used for all assay experiments.

HUVECs are pre-labeled with fluorescent agent Calcein AM and seeded in Extracellular Matrix coated 96-well culture plate with their full growth medium. After about four hours of the morphogenesis process, the endothelial capillary tubes should be formed. Then, test agent in designed doses of 50 μl volume is applied into the formed capillary tubule cultures as treatment conditions. The no-treatment controls can be added with vehicle of test agents. Sutent, a FDA approved anti-angiogenic drug one concentration can be included as assay performance control. After about six hours of treatment, the endothelial tubule morphology in each well is examined by microscopy, imaged, and the capillary disrupting activities under treatment conditions can be quantitatively analyzed. Each test conditions can be conducted in duplicate wells, including controls.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. An oil-in-water emulsion for reducing wrinkles and increasing skin penetration on the skin of a human in need thereof, the emulsion comprising therapeutically effective amounts of dimethyl isosorbide, pentylene glycol, ethoxydiglycol, propylene glycol, *Acmella oleracea* extract,

*Lavandula stoechas* extract, *Rosmarinus officinalis* leaf extract, and ethanol to reduce wrinkles and increasing skin penetration on the skin of the human.

2. The emulsion of claim 1, wherein the emulsion comprises 0.02% to 2% by weight of *Acmella oleracea* extract, 0.01% to 1% by weight of *Lavandula stoechas* extract, and 0.005% to 0.5% by weight of *Rosmarinus officinalis* leaf extract.

3. The emulsion of claim 1, wherein each of the extracts are individually an aqueous extract, an alcohol extract, a polyol extract, or a combination thereof.

4. The emulsion of claim 1, wherein:

the *Rosmarinus officinalis* leaf extract is obtained with a fluid extraction solvent mixture comprising betaine, lactic acid, and water;

the *Lavendula stoechas* extract is a *Lavendula stoechas* flower/leaf/stem extract obtained with a supercritical carbon dioxide extraction solvent; and the *Acmella oleracea* extract is obtained with a fluid extraction solvent mixture comprising water, ethanol, and 1,3 propanediol.

5. The emulsion of claim 1, wherein the emulsion comprises:

5% to 15% by weight of ethanol;

5% to 15% by weight of dimethyl isosorbide;

3% to 7% by weight of pentylene glycol;

1% to 5% by weight of ethoxydiglycol; and

1% to 5% by weight of propylene glycol.

6. The emulsion of claim 1, wherein the emulsion comprises 30% to 60% by weight of water.

7. The emulsion of claim 1, wherein the emulsion further comprises:

cetyl esters;

stearyl alcohol;

cetearyl olivate;

sorbitan olivate;

acrylates/C10-30 alkyl acrylate crosspolymer;

cetyl palmitate; and sorbitan palmitate.

8. The emulsion of claim 7, wherein the emulsion comprises:

3% to 7% by weight of cetyl esters;

1% to 5% by weight of stearyl alcohol;

1% to 5% by weight of cetearyl olivate;

1% to 5% by weight of sorbitan olivate;

0.1% to 1% by weight of acrylates/C10-30 alkyl acrylate crosspolymer;

0.1% to 1% by weight of cetyl palmitate; and 0.1% to 1% by weight of sorbitan palmitate.

9. A method of reducing wrinkles and increasing skin penetration in a human in need thereof comprising topically applying the emulsion of claim 1 to the human's skin, wherein the emulsion reduces a wrinkle and increases skin penetration of the human's skin.

10. The method of claim 9, wherein the emulsion is applied to a fine line and/or the wrinkle on the human's skin.

11. The method of claim 10, wherein appearance of the fine line and/or the wrinkle on the human's skin is reduced after topical application of the emulsion to the human's skin.

12. The method of claim 11, wherein the emulsion reduces muscle contraction of a muscle that causes the appearance of the fine line or the wrinkle on the human's skin.

13. The method of claim 12, wherein the muscle is a glabellar complex muscle, an orbicularis oculi muscle, a depressor muscle, a *frontalis* muscle, or any combination thereof.

14. The method of claim 10, wherein the fine line and/or the wrinkle is a rhytide.

15. The method of claim 9, wherein:

the *Acmella oleracea* extract stimulates collagen production and laminin production in the human's skin; and the *Rosmarinus officinalis* leaf extract reduces matrix metalloproteinases 1, 3, or 9 production in the human's skin.

16. The method of claim 9, wherein the skin is forehead skin, cheek skin, chin skin, and/or orbital area skin.

* * * * *